United States Patent
Myslinski

(10) Patent No.: US 10,463,298 B1
(45) Date of Patent: *Nov. 5, 2019

(54) DEVICE, METHOD AND SYSTEM FOR IMPLEMENTING A PHYSICAL AREA NETWORK FOR CANCER IMMUNOTHERAPY

(71) Applicant: Lucas J. Myslinski, Sunnyvale, CA (US)

(72) Inventor: Lucas J. Myslinski, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,049

(22) Filed: Apr. 2, 2019

Related U.S. Application Data

(63) Continuation of application No. 16/217,358, filed on Dec. 12, 2018, now Pat. No. 10,265,017.

(51) Int. Cl.
| | | |
|---|---|---|
| *A61B 5/00* | (2006.01) | |
| *A63F 13/212* | (2014.01) | |
| *H04B 10/90* | (2013.01) | |
| *A61B 5/07* | (2006.01) | |
| *H04B 13/00* | (2006.01) | |
| *A61K 41/00* | (2006.01) | |

(52) U.S. Cl.
CPC .......... *A61B 5/4839* (2013.01); *A61B 5/0024* (2013.01); *A61B 5/07* (2013.01); *A61K 41/00* (2013.01); *A63F 13/212* (2014.09); *H04B 10/90* (2013.01); *H04B 13/005* (2013.01); *A61B 2562/0285* (2013.01)

(58) Field of Classification Search
CPC ....... A61B 5/4839; A61B 5/0024; A61B 5/07; A61B 2562/0285; A61K 41/00; H04B 13/005; H04B 10/90; A63F 13/212
See application file for complete search history.

(56) References Cited

U.S. PATENT DOCUMENTS

| | | | |
|---|---|---|---|
| 9,320,465 B2 | 4/2016 | Kline | |
| 9,687,182 B2 | 6/2017 | Bode et al. | |
| 2004/0122315 A1 | 6/2004 | Krill | |
| 2007/0227273 A1* | 10/2007 | Layton | G01Q 30/20 73/865.8 |
| 2008/0146890 A1 | 6/2008 | LeBoeuf | |
| 2008/0149832 A1* | 6/2008 | Zorn | B82Y 35/00 250/311 |
| 2013/0337066 A1* | 12/2013 | Zhang | A61K 39/0011 424/489 |
| 2014/0278510 A1 | 9/2014 | McLean | |
| 2015/0065821 A1 | 3/2015 | Conrad | |
| 2018/0200194 A1* | 7/2018 | Bhujwalla | A61K 9/0019 |

OTHER PUBLICATIONS

Robert Lamb, How Electronic Tattoos Work, https://electronics.howstuffworks.com/gadgets/other-gadgets/electronic-tattoo.htm/printable (accessed Dec. 1, 2018).

(Continued)

*Primary Examiner* — Theodore J Stigell
(74) *Attorney, Agent, or Firm* — Haverstock & Owens LLP

(57) ABSTRACT

A physical area network described herein enables significantly improved health monitoring and treatment by utilizing internal (in-body) mechanisms and information and external mechanisms and information.

8 Claims, 13 Drawing Sheets

(56) References Cited

OTHER PUBLICATIONS

Fabio Bergamin, Demystifying nanocrystal solar cells, https://www.ethz.ch/en/news-and-events/eth-news/news/2015/01/demystifying-nanocrystal-solar-cells.html (Jan. 27, 2015).
New solar power nanotechnology material converts 90 percent of captured light into heat, https://www.nanowerk.com/nanotechnology-news/newsid=37903.php (Oct. 29, 2014).
Hakim Mabed, Enhanced Spread in Time On-Off Keying Technique for Dense Terahertz Nanonetworks, https://publiweb.femto-st.fr/tntnet/entries/14160/documents/author/data, Femto-ST institutes, University of Bourgogne Franche-Comte (accessed Dec. 1, 2018).
Elayan et al., In Vivo Communication in Wireless Body Area Networks, Springer Book Information and Technological Innovations for Smart Cities (Dec. 2016).
Prachi Patel, A Nano Pressure Sensor, https://www.technologyreview.com/s/407439/a-nano-pressure-sensor/ (Mar. 6, 2007).
Chemical and Biological Sensors Using Nanotechnology, http://www.understandingnano.com/sensor.html (accessed Dec. 1, 2018).
Nanosensor, https://en.wikipedia.org/wiki/Nanosensor (accessed Oct. 24, 2018).
Qureshi et al., Utility of DNA methylation markers for diagnosing cancer, International Journal of Surgery, vol. 8, Issue 3, 2010, pp. 194-198 (2010).
Tsou et al., DNA methylation analysis: a powerful new tool for lung cancer diagnosis, NPG, Oncogene, 21, 5450-5461 (2002).
Kang et al., CancerLocator: non-invasive cancer diagnosis and tissue-of-origin prediction using methylation profiles of cell-free DNA, https://genomebiology.biomedcentral.com/articles/10.1186/s13059-017-1191-5, Genome Biology (2017).
Nlayyar et al., Internet of Nano Things (IoNT): Next Evolutionary Step in Nanotechnology, http://article.sapub.org/10.5923.j.nn.20170701.02.html (accessed Nov. 20, 2017).
Tracy, Phillip, What is the internet of things at nanoscale?, https://www.rcrwireless.com/20160912/big-data-analytics/nano-scale-iot-tag31-tag99 (Sep. 12, 2016).
Garcia-Martinez, Javier, The Internet of Things Goes Nano, https://www.scientificamerican.com/article/the-internet-of-things-goes-nano/ (Jun. 23, 2016).
Lima, Joao, 5 out of this world nanotechnologies driving future IoT, https://www.cbronline.com/internet-of-things/5-out-of-this-world-nanotechnologies-driving-future-iot-4671393/ (Sep. 17, 2015).
Cuffari, Benedette, Nanotechnology in 2017: The Story so Far Jan.-May, https://www.azonano.com/article.aspx?ArticleID=4443, (Apr. 4, 2017).
Diamandis, Peter, Nanorobots: Where We Are Today and Why Their Future Has Amazing Potential, https://singularityhub.com/2016/05/16/nanorobots-where-we-are-today-and-why-their-future-has-amazing-potential/#sm.001sk48c3pmxfbe10j91wmczrhcc8 (May 16, 2016).
Singh, Pawan, Internet of Things Based Health Monitoring System : Opportunities and Challenges, International Journal of Advanced Research in Computer Science, vol. 9, No. 1 (Jan.-Feb. 2018).
Sun et al., Security and Privacy in the Medical Internet of Things: A Review, Security and Communication Networks, vol. 2018, Article ID 5978636, 9 pages, https://doi.org/10.1155/2018/5978636 (Jan. 12, 2018).
Sharma et al., An Enhanced-Simple Protocol for Wireless Body Area Networks, Journal of Engineering Science and Technology vol. 13, No. 1 (2018) 196-210, School of Engineering, Taylor's University (2018).
Patel and Wang, Applications, Challenges, and Prospective in Emerging Body Area Networking Technologies, IEEE Wireless Communications, (Feb. 2010).
Barakah and Ammad-uddin, A Survey of Challenges and Applications of Wireless Body Area Network (WBAN) and Role of a Virtual Doctor Server in Existing Architecture, 2012 Third International Conference on Intelligent Systems Modelling and Simulation, IEEE 2012. (2012).
What Are Nanorobots?, http://www.tech-faq.com/nanorobots.html (accessed Jul. 19, 2018).
I.F. Akyildiz, Internet of µThings, Nanothings & Bio-Nanothings, https://bwn.ece.gatech.edu/.../Internet%20of%20Nanothings%202017-04.pdf (Accessed Dec. 1, 2018).
Nealon, Cory, Tiny graphene radios may lead to Internet of Nano-Things, http://www.buffalo.edu/news/releases/2016/11/002.html (Nov. 1, 2016).
Dabhi et al., Internet of Nano Things—The Next Big Thing, International Journal of Engineering Science and Computing, (Apr. 2017).
Horimoto et al., Emerging roles of the tumor-associated stroma in promoting tumor metastasis, Cell Adhesion & Migration 6:3, 193-202; May/Jun. 2012.
Eyden, B., The myofibroblast: phenotypic characterization as a prerequisite to understanding its functions in translational medicine, https://www.ncbi.nlm.nih.gov/pmc/articles/PMC3823470/, J Cell Mol Med. Jan. 12, 2008(1): 22-37, (published Dec. 25, 2007).
Fang et al., Cancer Cell Membrane-Coated Nanoparticles for Anti-cancer Vaccination and Drug Delivery, Nano Letter, 14(4): 2181-2188 (Apr. 9, 2014).
Nimmagadda et al., Molecular Imaging of CXCR4 Receptor Expression in Human Cancer Xenografts with [64Cu] AMD3100-Positron Emission Tomography, Cancer Res. 2010; 70(1):3935-4.
Krishnamachary et al., Hypoxia Regulates CD44 and Its Variant Isoforms through HIF-1a in Triple Negative Breast Cancer, PLoS ONE 7(8): e44078. doi:10.1371/journal.pone.0044078 (Aug. 28, 2012).
Hu et al., A biomimetic nanosponge that absorbs pore-forming toxins, Nature Nanotechnology, 8(5):336-40 (2013).
Fang et al., Lipid-insertion enables targeting functionalization of erythrocyte membrane-cloaked nanoparticles, Nanoscale, 5(19):8884-8 (2013).
Hu et al., Polymeric nanotherapeutics: clinical development and advances in stealth functionalization strategies, Nanoscale, 6(1):65-75 (2014).
Luk et al., Interfacial Interactions between Natural RBC Membranes and Synthetic Polymeric Nanoparticles, Nanoscale, 6(5):2730-2737 (2014).
Lounis et al., Healing on the cloud: Secure cloud architecture for medical wireless sensor networks, Future Generation Computer Systems, vol. 55, pp. 266-277 (2016).
Bezawada et al., Privacy Preserving String Matching for Cloud Computing, Proceedings of the 35th IEEE International Conference on Distributed Computing Systems, ICDCS '15, pp. 609-618 (Jul. 2015).
U.S. Appl. No. 62/778,427 (by Myslinski, filed Dec. 12, 2018).
U.S. Appl. No. 62/778,433 (by Myslinski, filed Dec. 12, 2018).
U.S. Appl. No. 62/778,436 (by Myslinski, filed Dec. 12, 2018).
Notice of Allowance from U.S. Appl. No. 16/217,358.

* cited by examiner

DEVICE, METHOD AND SYSTEM FOR IMPLEMENTING A PHYSICAL AREA NETWORK FOR CANCER IMMUNOTHERAPY

CROSS-REFERENCE TO RELATED APPLICATION(S)

This application is a continuation application of U.S. patent application Ser. No. 16/217,358 (now U.S. Pat. No. 10,265,017), filed on Dec. 12, 2018, and titled "DEVICE, METHOD AND SYSTEM FOR IMPLEMENTING A PHYSICAL AREA NETWORK FOR CANCER IMMUNOTHERAPY," which is hereby incorporated by reference in its entirety for all purposes.

FIELD OF THE INVENTION

The present invention relates to the field of networking. More specifically, the present invention relates to the field of networks associated with the human body.

BACKGROUND OF THE INVENTION

Several companies have developed wearable devices which are able to monitor health information such as heart rate. However, these devices have many limitations.

SUMMARY OF THE INVENTION

A physical area network described herein enables significantly improved health monitoring and treatment by utilizing internal (in-body) mechanisms and information and external mechanisms and information.

DETAILED DESCRIPTION OF THE PREFERRED EMBODIMENT

A physical area network, also referred to as a Body Area Network (BAN), Wireless BAN (WBAN), or a Body Sensor Network (BSN), is a network of wearable and/or implantable devices used to cooperate with additional devices to provide further collection, analysis and output/effects related to body information. A physical area network is described herein. The physical area network is able to utilize implementations such as the Internet of Things (IoT), the Internet of MicroThings (IoµT) and the Internet of NanoThings (IoNT). Although nanonodes are described herein, where applicable, micronodes are able to be implemented instead or in addition.

Body information (and other information) is able to be collected using wearable devices, internal devices (e.g., implanted, ingested, injected, inhaled), and/or other devices.

Figure 1:
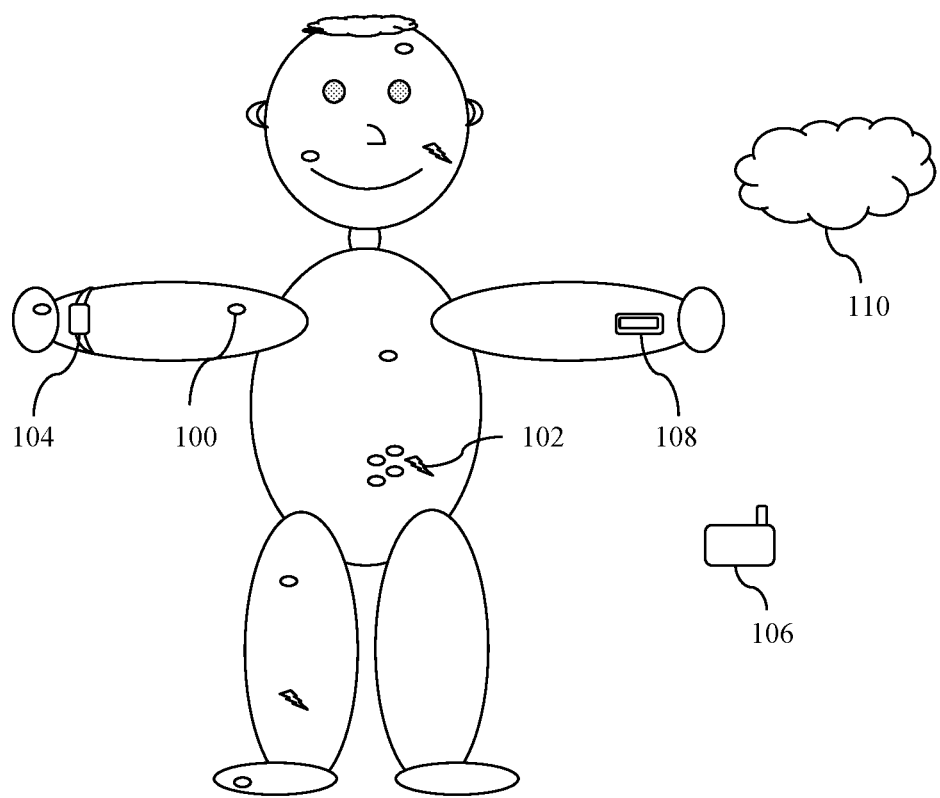
FIG. 1 illustrates a diagram of a network architecture for a physical area network according to some embodiments.

FIG. 1 illustrates a diagram of a network architecture for a physical area network according to some embodiments. The physical area network includes one or more nano-nodes 100, one or more nano-routers 102, one or more nano-micro interfaces 104, and/or one or more control units 106. In some embodiments, fewer or additional components are utilized. In some embodiments, the physical area network includes one or more electronic tattoos 108. In some embodiments, the physical area network is able to communicate via a network 110 (e.g., the Internet, a cellular network, or an intranet) or using peer-to-peer communication.

In the exemplary FIG. 1, the small circles or dots represent one or more nano-nodes 100, the lightning bolts represent one or more nano-routers 102, the smart watch represents a nano-micro interface 104 and the router represents one or more control units 106. As shown in the example, the nano-nodes 100 are able to be inside of a user such as in the cranium, on a tooth, in the blood stream going to the arm and hands, heart, legs, gut and/or any other body part, and/or in any other body part. Similarly, the nano-routers 102 are able to located anywhere internally. In some embodiments, the nano-nodes 100 and/or nano-routers 102 are able to be positioned in specific locations of the body (e.g., muscles, bones, ligaments, digestive system, lungs, blood/cardiovascular system, nervous system/brain/spinal cord, skin, any other system/body part) to monitor varying aspects of the body. In some embodiments, the nano-nodes 100 and/or nano-routers 102 are able to move (e.g., through the digestive tract, the bloodstream, and/or any other body part/system). The nano-nodes 100 and/or nano-routers 102 are also able to be positioned externally such as on clothing (e.g., hat, glasses, headband, mask, scarf, shirt, jacket, gloves, underwear, pants, socks, footwear/sneakers/shoes), jewelry, or sporting equipment (e.g., a baseball bat, glove, golf club, tennis racket, football, baseball, hockey stick, puck, soccer ball, tennis ball, golf ball, basketball, or any other sporting equipment). The nano-macro interfaces 104 are also able to be internal or externally located (e.g., as a wearable watch, jewelry, clothing, eyeglasses/sunglasses/eyewear, contact lenses, headgear, band-aid, bandage, equipment). Although the example shows only a few components, an actual physical area network is able to potentially include millions or more components (e.g., millions, billions or trillions of nano-nodes throughout the body). Similarly, in simpler systems, the physical area network is able to be a single component such as a single nano-node or a few components such as a single nano-node, nano-router and nano-micro interface.

The one or more nano-nodes 100 are nano machines which perform tasks such as detecting health issues (e.g., cancer, high blood pressure, low/high blood sugar, flu/cold, virus, bacteria, cardiovascular disease, digestive issues, respiratory issues, allergies, auto-immune diseases, neurological problems) and/or others. The nano-nodes 100, nano-routers 102 and/or nano-micro interfaces 104 are able to acquire health information such as blood pressure, pulse rate, respiration rate, temperature, and/or any other information. The nano-nodes 100 are also able to be used to treat medical issues such as delivering antibiotics/medication to a localized position, provide insulin, repair an injury, unclog a blockage (e.g., remove arterial plaque), block/disrupt cancer communications, treat/attack cancer cells, and/or any other treatment options. Nano-nodes 100 are able to include biological sensors positioned in the human body. The nano-nodes 100 are able to be utilized in the fields/technologies of surgery, prosthetics, artificial retina, cochlear implants, brain pacemakers, heart pacemakers, and many other implementations.

In some embodiments, the nano-nodes 100 are hybrid molecular/semiconductor electronics, nanotubes/nanowires, molecular electronics, and/or other implementations. For example, scientists at Lawrence Berkeley National Laboratory have developed a functional 1nm transistor. Therefore, a nano-device is able to be made using the 1nm transistor with any additional components which are also scaled down to size. U.S. Pat. Nos. 9,320,465 and 9,687,182, which are incorporated by reference in their entireties for all purposes, are examples of functioning nanodevices. In some embodiments, the nano-nodes 100 are biological elements. The nano-nodes 100 are able to implement a variety of functions such as sensing, moving, heating, cooling, cutting, attaching, attacking, detecting, carrying, disrupting, containing, and/or any other function described herein.

The nano-node 100 is able to comprise any material such as a metal oxide such as $Al_2O_3$, $In_2O_3$, MgO, ZnO, $CeO_2$, $CO_3O_4$, and/or $TiO_2$, a magnetic material, any other bioinert material, any biodegradable material, any biocompatible material, nanotubes, and/or any other appropriate material.

The nano-nodes 100 are able to be coated with a biocompatible material (metal) such as alumina, zirconia, alloys, poly ethylene glycol, and/or polytetrafluoroethylene-like materials of varying thickness such as a few nanometers to micrometers. The nano-nodes 100 are able to be packaged in insulating materials, water-vapor permeable materials, polymeric materials such as epoxies, urethanes, silicones, resins, Parylene, and others. The packaging is able to be a polymer including hydrophobic, hydrophilic, or amphipathic molecules, proteins, peptides, cell membrane components and/or other organic/biological components. The packaging is also able to be anti-microbial. In some embodiments, the nano-nodes 100 are coated/covered/surrounded with cells (e.g., the user's cells) to prevent the user's body from attacking.

In some embodiments, the nano-nodes 100 include one or more chambers which are individually or collectively accessible (e.g., by opening, removing, making permeable a barrier). The contained substance (e.g., agent, reagent, gas, medicine, chemical, biological material, vitamin, mineral, supplement, sugar, caffeine) in a chamber is released and/or pumped out. In some embodiments, the chambers contain neutral or inert agents when separate, but when combined with other agents, a reaction occurs. For example, a nano-node 100 includes agent X and agent Y which do nothing when contained in their separate chambers, but when released simultaneously, agent X and agent Y react and release energy, form a new agents, attack a specific substance/material, and/or have another type of reaction. In some embodiments, nano-nodes carry separate agents, for example, a first nano-node carries only agent X and a second nano-node carries only agent Y, and when the nano-nodes are in a close enough proximity to each other, their chambers release their respective agents such that the agents react. In some embodiments, the nano-nodes 100 are able to detect other nano-nodes 100 and only release the agents when the distance between each other is below a threshold. For example, determining the distance is below a threshold is by: a nano-node detects other nano-nodes by sending a signal (e.g., signal is only strong enough to reach within a threshold distance); electrical detection; motion detection; and/or any other way. In some embodiments, the nano-nodes 100 receive instructions from another device (e.g., the nano-micro interface 104) as to when to release the agent (and which agent if applicable). In some embodiments, the nano-nodes 100 release after a specified amount of time or at a specified time.

In some embodiments, hormones or hormone-inducing medication is able to be deployed using a nano-node 100. Similarly, insulin is able to be automatically released when a user's blood sugar is below a specified threshold. Proteins or protein-fragments are able to be carried and released to stimulate or inhibit reactions such as inducing or minimizing an immune system response. In another example, tiny particles of an allergen (e.g., peanut, wheat, pollen, pet dander, and so on) are introduced using a nano-device 100 to avoid/prevent/minimize allergic or auto-immune responses.

Similarly, in some embodiments, one or more sensors are located inside each chamber, but covered by the barrier/coating. Once the barrier/coating is removed/permeable, the sensors are able to detect anything such as chemicals, pH, presence of molecules, and/or other conditions in/near the chambers. Any other type of chamber is able to be included such as a waste chamber and/or energy chamber.

In some embodiments, the barrier dissolves/weakens/opens over time, and in some embodiments, a trigger (e.g., from the nano-micro interface 104, nano-node 100 and/or nano-router 102) occurs to dissolve/weaken/open the barrier.

The nano-node 100 is able to include one or more nano-pumps, one or more containers, other types of vessels, one or more nano-channels and/or any other components.

In some embodiments, a MEMS device is used to open/close mechanical doors to release the payload of the nano-node 100.

The nano-node 100 is able to include an integrated circuit controller unit for controlling on-chip sensing, measuring, controlling, moving and/or other functions/operations. The integrated circuit is able to include any computing components such as a processing core, a controller, cache memory, Random Access Memory (RAM), other types of memory/processing components, sensing/measuring components (temperature, pressure, light, heat, EM energy, water, chemical, biological, and others), communication components (e.g., antenna, receiver/transceiver devices), data buses, cargo (e.g., medicine, radioactive material), and/or any other components. Exemplary sensors include sensing/measuring oxygen, carbon dioxide, urea, hormones, ions, neurotransmitters, blood, proteins, chemicals, radiation, electricity, sensing rate of local tissue mitosis or changes. Furthering the example, the oxygen sensor is able to sense oxygen in a user's tissues. In another example, sensors are able to receive signals from nerve cells and transmit the signals via RF or sonic communications to other nerve cells (e.g., a nerve bridge). The nano-node 100 is able to measure tissue response employing the Doppler effect. Using the transmitter/receiver and/or sensors, the nano-node 100 is able to detect reflections of signals, phase shifts, and other signal changes (e.g., measuring deltas in velocities or phase shifts in signals of different wavelengths to analyze tissue state changes). The number of sensors on the chip is able to be application specific or general and can be as few as 1 to many thousands or more. In some embodiments, all of the components are able to process/communicate in real-time (e.g., transmit real-time sensor measurement information) to the nano-micro interface 104. The transceiver is able to utilize very low power EM function using varying frequencies such as very low, ultra high, terahertz or any other (e.g., more or less than 10,000 Hz; 5,000 Hz; 1,000 Hz). In some embodiments, communications are based on the IEEE 802.x protocol or IEEE 802.15.6 protocol.

As described in U.S. Pat. No. 9,687,182, the sensors are also able to detect: a pH value, a charge (e.g. of an ion or a polyelectrolyte), a temperature, a mass, an aggregation state, water content, hematocrit value, and/or a presence or absence and/or a quantity of an analyte or other substance (such as a fat, a salt, an ion, a polyelectrolyte, a sugar, a nucleotide, DNA, RNA, a peptide, a protein, an antibody, an antigen, a drug, a toxin, a hormone, a neurotransmitter, a metabolic product, and/or any other analyte of interest), any biomarkers which form a variable component of the human or animal body, such as albumins/globulins, alkaline phosphatase, alpha-1-globulin, alpha-2-globulin, alpha-1-antitrypsin, alpha-1-fetoprotein, alpha-amylases, alpha-hydroxybutyrate-dehydrogenase, ammonia, antithrombin III, bicarbonate, bilirubin, carbohydrate antigen 19-9, carcinoembryonic antigens, chloride, cholesterol, cholinesterase, cobalamin/vitamin B12, coeruloplasmin, C-reactive proteins, cystatin C, D-dimers, iron, erythropoetin, erythrocytes, ferritin, fetuin-A fibrinogen, folic acid/vitamin B9, free tetrajodthyronine (fT4), free trijodthyronine (fT3), gamma-glutamyl transferase, glucose, glutamate dehydrogenase, glutamate oxaloacetate transaminase, glutamate pyruvate transaminase, glycohemoglobin, hematocrit, hemoglobin, haptoglobin, uric acid, urea, HDL cholesterol, homocysteine, immunoglobulin A, immunoglobulin E, immunoglobulin G, immunoglobulin M, INR, calium, calcium, creatinine, creatine kinase, copper, lactate, lactate dehydrogenase, LDL cholesterol, leukocytes, lipase, lipoprotein, magnesium, corpuscular hemoglobins, myoglobin, sodium, NT-proBNP/BNP, phosphate, prostate-specific antigens, reticulocytes, thrombocytes, transferrin, triglycerides, troponin T, or drugs such as muscarinic receptor antagonists, neuromuscular blocking substances, cholesterol esterase inhibitors, adrenoceptor agonists, indirectly acting sympathomimetics, methylxanthine, alpha-adrenoreceptor antagonists, ergot alkaloids, beta-adrenoceptor antagonists, inactivation inhibitors, antisympathonics, 5-HT receptor agonists, histamine receptor agonists, histamine receptor antagonists, analgesics, local anesthetics, sedatives, anticonvulsants, convulsants, muscle relaxants, antiparkinsonians, neuroleptics, antidepressants, lithium, tranquilizers, immunsuppressants, antirheumatics, antiarrhythmics, antibiotics, ACE inhibitors, aldosterone receptor antagonists, diuretics, vasodilatators, positive inotropic substances, antithrombotic/thrombolytic substances, laxatives, antidiarrheal agents, pharmaceuticals for adiposity, uricostatics, uricosurics, antilipemics, antidiabetics, antithypoglycemia, hormones, iodized salts, threostatics, iron, vitamins, trace elements, virostatics, antimycotics, antituberculotics, and substances for tumor chemotherapy. However, any other item for detection can be detected by the sensor system. The item preferably relates to a variable component of the animal body and/or human body.

In some embodiments, detecting/sensing utilizes a receptor or receptor layer that causes a measurable reaction with the item to be measured. Exemplary receptors are peptides, proteins, enzymes, antibodies and fragments, RNA, DNA, nucleotides, fats, sugars, salts, ions, cyclic macromolecules, and any other suitable substances.

The nano-node 100 and/or nano-routers 102 are able to be injected, implanted, ingested, inhaled, attached/affixed (e.g., on a tooth, dental filling), applied transdermally, and/or any other method of application.

In some embodiments, a nano-node 100 becomes stationary (e.g., injected/implanted into muscle or attaches to a body wall), and measures body temperature, pressure, chemical/biological/biochemical concentrations and/or other information, and the acquired information is communicated to the nano-micro interface 104 (via one or more nano-nodes 100 and/or one or more nano-routers 102).

In some embodiments, a nano-node 100 is mobile, capable of moving within the user's body (e.g., in blood, lymph or other bodily fluid). The nano-node 100 is configured such that it will not cause a blockage (e.g., fewer than 5 microns in diameter in any direction). When a nano-node 100 does not have its own power source (e.g., battery), power is continuously acquired by the nano-node 100 through induction, RF coupling, or another means, or the nano-node 100 does not acquire energy.

In some embodiments, the nano-nodes 100 include body-coupled communications transceivers capacitively coupled to the skin and use the human body as a channel to communicate information.

In some embodiments, the nano-nodes 100 each have a specific purpose (e.g., nano-nodes for sensing, nano-nodes for communicating, and nano-nodes for deploying medication). For example, the nano-nodes for sensing and/or medication have limited communication capabilities (e.g., 1-way communications). In some embodiments, the nano-nodes 100 are able to perform multiple tasks. In some embodiments, the physical area network includes a variety of specific purpose nano-nodes.

As described herein, the nano-node 100 is able to function by itself or collectively with other devices (e.g., other nano-nodes 100 or other devices).

As described herein, the nano-micro interface 104 is able to be any external device such as a smart watch, smart clothing, smart jewelry, a smart phone and/or any other computing device. In some embodiments, the nano-micro interface 104 includes a display for showing a Graphical User Interface (GUI), a voice-activated system, and/or any other interface. The GUI is able to be configured specifically for the physical area network including text, icons and/or alerts (visual/audible) specific to the physical area network. The nano-micro interface 104 is also able to display video and/or any other content. In some embodiments, the voice-activated system recognizes a users voice, and only accepts commands from recognized/permitted users.

In some embodiments, the nano-micro interface 104 includes an optical sensor (e.g., CMOS, CCD, photodiode), acoustic sensor (e.g., piezoelectric, piezoceramic), electro-chemical sensor (voltage, impedance), thermal sensor, mechanical sensor (e.g., pressure, strain), magnetic sensor, and/or electromagnetic sensor (e.g., RF, magnetic resonance).

In some embodiments, the physical area network includes a control unit 106. In some embodiments, the control unit 106 controls aspects of the BAN such as the nano-nodes and nano-routers. In some embodiments, a wearable device such as a smart watch includes/is the control unit 106. In some embodiments, the control unit 106 is not a wearable device and is a stationary device such as a hub/router. The control unit 106 and/or another unit (e.g., sensor units) are able to acquire external information such as temperature, light, humidity, time, date, location, altitude, social networking information, and/or any other information. In some embodiments, the nano-micro interface 104 and the control unit 106 are or part of a wearable device such as a smart watch.

Figure 2:
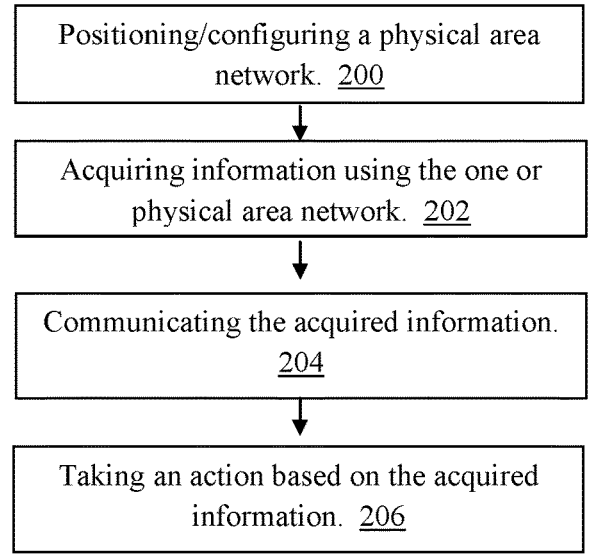
FIG. 2 illustrates a flowchart of implementing a physical area network according to some embodiments.

FIG. 2 illustrates a flowchart of implementing a physical area network according to some embodiments. In the step 200, a physical area network is positioned/configured. For example, nano-nodes and/or nano-routers are implanted, injected, inhaled, swallowed, attached, and/or otherwise positioned in place or positioned to enable the nano-nodes and/or nano-routers to move or be moved into a desired location. Furthering the example, some nano-nodes and/or nano-routers are stationary, some are able to be moved using an external source, and some are able to move autonomously. Additionally, a nano-micro interface is able to be positioned (e.g., a user wears a smart watch or puts on smart clothing). In some embodiments, configuration steps are implemented as well such as the nano-nodes communicating their position to enable a server device and/or the nano-micro interface to generate a map. Additionally, communications are able to be configured and/or any other configuration steps are able to be implemented. In the step 202, information is acquired using the physical area network. The information is able to be acquired using nano-nodes (e.g., using nano-sensors to detect substances/information) as described herein. The information is also able to be received from external devices (e.g., social network, medical study) to be used by the physical area network. In the step 204, the acquired information is communicated. For example, the nano-nodes communicate with each other and/or the nano-routers and/or the nano-micro interface (and/or another device). Similarly, the nano-micro interface is able to communicate external information/commands to the nano-routers and/or the nano-nodes. The communications are able to be implemented in any manner using various techniques for efficient, safe, and clear transmission. In the step 206, an action is taken based on the acquired information. The action is able to include displaying a message, sounding an alarm/alert, performing analysis, forwarding the information, providing/deploying medication, performing medical procedures, and/or any other action described herein. In some embodiments, fewer or additional steps are implemented. In some embodiments, the order of the steps is modified.

Cancer

A nano-node 100 (or nano-nodes) is/are implanted in or near a tumor/cancer site for real-time monitoring of treatment delivered directly to the tumor. In another example, multiple nano-nodes 100 are positioned around the tumor to detect treatment/spread of the tumor. For example, one or more nano-nodes 100 measure signal/reflections off the tumor, changes in electrical permittivity, magnetic permeability, turbidity, light transmission/reflection, blood/tumor marker concentrations, and/or any other information. Mitosis rate sensing is able to be implemented as well. Furthering the example, some of the nano-nodes are able to be treatment nodes which deliver medication/radiation to the cancer cells.

In some embodiments, the physical area network is implemented to provide cancer immunotherapy. In some implementations, the cancer immunotherapy is implemented as described in U.S. Patent Application Publication 2018/0200194 to Bhujwalla et al., titled, "DECOY NANOPARTICLES TO DISRPUT CANCER CELL-STROMAL CELL NETWORKS," which is hereby incorporated by reference in its entirety for all purposes.

Nano-nodes of the physical area network are able to be coated with plasma membrane derived from cancer cells. These plasma membrane-coated nano-nodes retain the membrane-associated components (lipids, proteins, and carbohydrates) in a native-like state within the cell membranes after isolation and translocation to the surface of nano-nodes where all components present in the right-side-out orientation. In some embodiments, the plasma membrane-coated nano-nodes replicate the complex surface of the cancer cell plasma membrane on the nano-node surface. This further allows the nano-nodes to act: (1) as decoys to misdirect cancer signaling or (2) as vaccines to activate the immune response to a user's cancer. In some embodiments, the nano-nodes are loaded with therapeutic cargoes or imaging reporters for treating or detecting cancer, respectively. In some embodiments, the compositions and methods described herein are used to treat cancer. Any type of cancer is able to be detected/treated such as breast cancer, skin cancer, lung cancer, brain cancer, pancreatic cancer, esophageal cancer, stomach cancer, liver cancer, kidney cancer, colorectal cancer, intestinal cancer, bladder cancer, prostate cancer, ovarian cancer, uterine cancer, testicular cancer, sarcoma, lymphoma, leukemia, retinoblastoma, oral cancer, bone cancer, neoplasia, dysplasia, and glioma.

Stromal cells such as cancer-associated fibroblasts (CAFs) mediate many of the aggressive characteristics of cancer (Horimoto Y, Polanska U M, Takahashi Y, Orimo A. Emerging roles of the tumor-associated stroma in promoting tumor metastasis. Cell Adh Migr. 2012; 6(3):193-202), but have an ever-replenishing supply that is largely left intact by current therapeutic strategies (Eyden B. The myofibroblast: phenotypic characterization as a prerequisite to understanding its functions in translational medicine. J Cell Mol Med. 2008; 12(1):22-37). Because of their important functional roles, destroying stromal cells that assist cancer cells is not a viable solution. Instead, as described herein, disrupting communications between cancer cells and stromal cells is a useful strategy. Nano-nodes that attach to CAFs and disrupt the CXCL12-CXCR4 axis are described herein, which has a wide spectrum of roles in facilitating breast cancer invasion and metastasis through breast cancer-CAF signaling.

Also provided is the functionalization of degradable poly (lactic-co-glycolic acid) (PLGA) polymeric nano-nodes with a layer of cell membrane derived from CXCR4-overexpressed U87MG (U87-CXCR4) cells to form a core-shell nanostructure (Fang, R. et al., Nano Lett. 2014, 14, 2181-2188). Because of the specific expression of alpha smooth muscle actin (α-SMA) on CAFs, the membrane-coated nano-nodes are labeled with antibodies against α-SMA to guide the nano-nodes to attach to CAFs and act as a nanosponge that absorbs CXCL12 secreted by CAFs.

Described herein is the coating of synthetic polymeric nano-nodes with plasma membranes derived from various cancer cells. The membrane-associated components (lipids, proteins, and carbohydrates) are retained in a native-like state within the cell membranes after isolation and translocation to the surface of nano-nodes where all components present in the right-side-out orientation. This biomimetic strategy provides the advantage of replicating the complex surface of the cancer cell plasma membrane profile on nano-nodes and consequently, this technology provides a robust means of using nano-nodes as, e.g., decoys to misdirect cancer cell signaling or as cancer vaccines that activate immune responses to an individual's cancer along with a capacity to carry a range of therapeutic cargoes or imaging reporters for cell-specific delivery applications.

Described herein is the harnessing of cancer cell plasma membranes as biologically functional coatings for polymeric nano-nodes. Cancer cell plasma membrane fractions possess a comprehensive array of antigens in native conformations, the complexity of which is unlikely to be duplicated by any synthetic chemistry or structural biology strategy. Being biomimetic means that these nano-nodes possess natural attributes of the host's biology and as such have stealth-like properties, e.g., less immunogenicity than antigen presentation approaches described previously. Recent advances have demonstrated the feasibility of coating nano-nodes with red blood cell membranes (RBCs) to mimic RBCs. However, described herein is technology that allows for coating of nano-nodes with specific biologically functional cancer cell membranes. The utility of these biomimetic nano-nodes is that they are loaded with, e.g., therapeutic cargos for cell-specific targeted treatments or they can be used to assist in the activation of the immune response against a cancer or to disrupt/abrogate fatal cancer cell signaling/survival. A distinct advantage is the use of a patient's cancer cells as the origin of the membranes for such strategies, which fully aligns with the concept of personalized medicine.

The biomimetic nano-node formulation technology includes or consists of two components: (1) the plasma membrane fractions (MFs) of cancer cells isolated under a sequential process of hypotonic lysing, Potter-Elvehj em homogenization and Percoll® density gradient centrifugation, which allows for the isolation of pure plasma MFs as flexible bilayer vesicles with an average size of approximately 200 nm; and (2) polymeric nano-nodes including or consisting of carboxy-terminated polylactic-co-glycolic acid (PLGA), an FDA-approved biodegradable polymer, which forms spherical negatively charged particles in the range of 40-60 nm through the processes of precipitation and evaporation. A far-red fluorescent dye, 1,1'-dioctadecyl-3,3,3',3'-tetramethylindodicarbocyanine, 4-chlorobenzenesulfonate salt (DiD, ex/em: 644 nm/665 nm) is incorporated into the PLGA core for fluorescently tracking nano-nodes. To generate biologically functional biomimetic nanoparticles, MFs and PLGA nano-nodes are mixed and subjected to physical extrusion through a polycarbonate porous membrane. The extrusion process creates a uniform unilamellar MF coating with a thickness of 5 nm encapsulating the PLGA nano-nodes. The mechanical force of the extrusion process guides the membrane-particle assembly while the electrostatic interaction between PLGA nano-nodes and MFs enables the efficient and complete translocation of the fully functional plasma membrane with all of its associated components onto the polymeric nano-node surface in a "right-side-out" manner. This facile membrane coating approach is scalable and highly reproducible. As noted above, the utility of these biomimetic nano-nodes is that they are loaded with, e.g., therapeutic cargos for cell-specific targeted treatments or they are used to assist in the activation of the immune response against a cancer or to disrupt/abrogate fatal cancer cell signaling/survival. A distinct advantage is the use of a patient's cancer cells as the origin of the membranes for such strategies, which fully aligns with the concept of personalized medicine.

In some embodiments, the physical area network implements one or more methods of treating cancer based on immunotherapy by inducing, enhancing or suppressing an immune system response. Immunotherapies such as activation immunotherapies or suppression immunotherapies are able to be implemented to use the immune system to treat cancer. Immunotherapies are able to be one or more of the following groups: cellular, antibody and cytokine. Immunotherapies exploit the subtle differences on the surfaces of the cancer cells (e.g., different molecules) which are able to be detected by the immune system and/or physical area network. The molecules are known as cancer antigens, which are typically proteins or carbohydrates. Immunotherapy is able to be used to induce/provoke the immune system into attacking the tumor cells by using the antigens as targets.

Antibody therapies are the most successful immunotherapy and can be used to treat a wide range of cancers. Antibodies are proteins produced by the immune system that bind to a target antigen on the cell surface. In normal physiology, the immune system uses antibodies to fight pathogens. Each antibody is specific to one or a few proteins. Those that bind to cancer antigens are used to treat cancer. Cell surface receptors, e.g., CD20, CD274, and CD279, are common targets for antibody therapies. Once bound to a cancer antigen, antibodies can induce antibody-dependent cell-mediated cytotoxicity, activate the complement system, or prevent a receptor from interacting with its ligand, all of which can lead to cell death. Multiple antibodies are approved to treat cancer, including Alemtuzumab, Ipilimumab, Nivolumab, Ofatumumab, and Rituximab.

Cellular therapies, also known as cancer vaccines, usually involve the removal of immune cells from the blood or from a tumor. Immune cells specific for the tumor are activated, cultured and returned to the patient where the immune cells attack the cancer. Cell types that can be used in this way are natural killer cells, lymphokine-activated killer cells, cytotoxic T cells and dendritic cells. In some embodiments, the physical area network assists in attacking the cancer. For example, the nano-nodes deliver medication to the cancerous cells in addition to the performing immunotherapy. In another example, the nano-nodes monitor the progress of the cancer (e.g., by detecting certain chemical triggers or detecting a physical mass). In another example, the nano-nodes monitor the immune system (response) by detecting certain chemical/biological levels in the blood.

Interleukin-2 and interferon-α are examples of cytokines, proteins that regulate and coordinate the behavior of the immune system. They have the ability to enhance anti-tumor activity and thus can be used as cancer treatments. Interferon-α is used in the treatment of hairy-cell leukemia, AIDS-related Kaposi's sarcoma, follicular lymphoma, chronic myeloid leukemia and malignant melanoma. Interleukin-2 is used in the treatment of malignant melanoma and renal cell carcinoma.

Decoys are often employed to achieve distraction or misdirection. The development of decoy nano-nodes that distract or misdirect cancer cells or cancer-associated stromal cells results in a disruption of interactions between cancer cells and stromal cells. In some embodiments, the physical area network provides for the development of biomimetic nano-nodes comprising or consisting of FDA approved poly(lactic-co-glycolic acid) PLGA, covered with cancer cell membranes to act as decoys to misdirect or distract cancer cells, or cancer-associated stromal cells. Once developed and characterized, the nano-nodes are evaluated for their ability to attach to cancer cells, and activated fibroblasts in circulation, and at primary or distant tumor sites. In some cases, the nano-nodes are decorated with an imaging reporter to characterize their biodistribution in vivo and ex vivo. Such nano-nodes have not been previously developed for applications in cancer. In an example, the nano-nodes attract circulating cancer cells, circulating stromal cells, and/or disrupt the spontaneous or experimental metastatic cascade in triple negative breast cancer (TNBC). Stromal cells such as cancer-associated fibroblasts (CAFs) mediate many of the aggressive characteristics of cancer (Horimoto Y, Polanska U M, Takahashi Y, Orimo A. Emerging roles of the tumor-associated stroma in promoting tumor metastasis. Cell Adh Migr. 2012; 6(3):193-202), but have an ever-replenishing supply that was largely left intact by therapeutic strategies prior (Eyden B. The myofibroblast: phenotypic characterization as a prerequisite to understanding its functions in translational medicine. J Cell Mol Med. 2008; 12(1):22-37) (Eyden B, Banerjee S S, Shenjere P, Fisher C. The myofibroblast and its tumours. J Clin Pathol. 2009; 62(3):236-49). Therefore, even following surgery or chemotherapy, a few surviving cancer cells that ordinarily would not survive on their own continue to have a host of stromal cells to assist them in reestablishment, either at the primary site or at a distant site. Because of their important functional roles, destroying stromal cells that assist cancer cells is not a viable solution in some embodiments. Instead, as described herein, disrupting communications between cancer cells and stromal cells is a useful strategy. TNBCs are the most lethal breast cancers and have limited treatment options. Since the CXCL12-CXCR4 axis has a wide spectrum of roles in facilitating breast cancer invasion and metastasis through breast cancer cell-CAF signaling, the role of high and low CXCR4 expressing cancer cell membrane-coated nano-nodes in disrupting cancer cell-CAF interactions is investigated as described. CAFs also play a major role in the formation of collagen 1 (Col1) fibers in tumors. Therefore, the functional effects of these nano-nodes on Col1 fiber patterns in primary and metastatic tumors are also evaluated. In some embodiments, such nano-nodes are loaded with a therapeutic cargo for targeting the premetastatic niche or eliminating circulating cancer cells, or they are used to assist in the activation of the immune response. These nano-nodes are also labeled with magnetic resonance (MR) contrast agents or radiolabeled for detection using human MR or positron emission tomography (PET) scanners. These studies identify new, clinically translatable strategies to disrupt the metastatic cascade in breast cancer, and represent a new strategy in developing effective treatments to prevent metastatic breast cancer.

The physical area network provides for the development and characterization of cancer cell membrane covered nano-nodes that contain an optical imaging reporter. Cancer cell membranes from triple negative metastatic DU4475 and MDA-MB-231 human breast cancer cells are used in these studies. The physical area network also provides for the evaluation of the interaction between the developed nano-nodes and fibroblasts and cancer cells in terms of migration and binding in culture, and the determination of the effects on tumor growth, Col1 fiber formation, and metastasis.

As described herein, decoy nano-nodes covered with cancer cell membranes mimic cancer cells and disrupt cancer cell-stromal cell interactions, reduce Col1 fiber formation in primary and metastatic tumors, and decrease the establishment of breast cancer metastasis.

Two triple (ER/PR/HER2) negative human breast cancer cell lines, DU4475 and MDA-MB-231 with high and low CXCR4 receptor expression (Nimmagadda S, Pullambhatla M, Stone K, Green G, Bhujwalla Z M, Pomper M G. Molecular imaging of CXCR4 receptor expression in human cancer xenografts with [64Cu]AMD3100 positron emission tomography. Cancer Res. 2010; 70(10):3935-4) are selected for these studies. In addition, MDA-MB-231 cells express the CD44 antigen (Krishnamachary B, Penet M F, Nimmagadda S, Mironchik Y, Raman V, Solaiyappan M, Semenza G L, Pomper M G, Bhujwalla Z M. Hypoxia regulates CD44 and its variant isoforms through HIF-1alpha in triple negative breast cancer. PLoS One. 2012; 7(8): e44078), a marker associated with stem-like breast cancer cells (Angeloni V, Tiberio P, Appierto V, Daidone M G. Implications of stemness-related signaling pathways in breast cancer response to therapy. Seminars in cancer biology. (2014), that provide additional validation of cell membrane integrity. Cancer cells from these two cell lines are used to form membrane vesicles to coat the nano-nodes. The nano-nodes also contain an imaging reporter.

Also provided are injectable nano-nodes to disrupt the establishment of breast cancer metastasis in humans. Biocompatibility is important, making the use of biomimetic nano-nodes relevant. For example, the patient's own cancer cells are used to synthesize the nano-nodes for personalized medicine. Following nano-node synthesis, characterization of toxicity, binding, stability and functional effects are performed in a culture. Studies assist in identifying optimum doses for in vivo characterization that determine the effects of nano-nodes on tumor growth, metastasis, Col1 fiber formation, and the presence of CAFs. The potential use of these nano-nodes in identifying the premetastatic niche has also been evaluated. Because of the critically important roles of stromal cells in several functions including the establishment of metastasis, strategies that disrupt the communications between cancer cells and stromal cells without destroying them provide solutions to prevent them from assisting cancer cells to survive, invade, and metastasize. In some cases, such nano-nodes also carry targeting peptides and molecular reagents such as complementary deoxyribonucleic acid (cDNA) and small interfering ribonucleic acid (siRNA) to act as multiple signaling disruptors against a spectrum of stromal cells to disrupt cancer cell survival and the establishment of metastasis.

Also provided are decoy nano-nodes that disrupt the interactions between cancer cells and stromal cells in an effort to define biomembrane coated-nano-node-based strategies to prevent or attenuate breast cancer metastasis.

Recent advances in polymeric nanoparticles camouflaged in cellular membranes have paved the way for entirely new strategies in cancer (Hu C M, Fang R H, Copp J, Luk B T, Zhang L. A biomimetic nanosponge that absorbs pore-forming toxins. Nature nanotechnology. 2013; 8(5):336-40) (Fang R H, Hu C M, Chen K N, Luk B T, Carpenter C W, Gao W, Li S, Zhang D E, Lu W, Zhang L. Lipidinsertion enables targeting functionalization of erythrocyte membrane-cloaked nanoparticles. Nanoscale. 2013; 5(19):8884-8) (Hu C M, Fang R H, Luk B T, Zhang L. Polymeric nanotherapeutics: clinical development and advances in stealth functionalization strategies. Nanoscale. 2014; 6(1): 65-75) (Luk B T, Jack Hu C M, Fang R H, Dehaini D, Carpenter C, Gao W, Zhang L. Interfacial interactions between natural RBC membranes and synthetic polymeric nanoparticles. Nanoscale. 2014; 6(5):2730-2737). These advances have demonstrated the feasibility of coating nano-nodes in a 'right-side' out manner using red blood cell (RBC) membranes to mimic RBCs, and act as nanosponges for toxins. Described herein are nano-nodes coated with cancer cell membranes, initially to act as nanosponges for CXCL12 in studies, and to act as potential decoys. The major advantage is that the patient's cancer cells can be cultured and used for such strategies. If these nano-nodes arrive at a premetastatic niche, they are also used to disrupt this niche, by carrying molecular targeting agents to prevent metastasis. The nano-nodes also enhance immunotherapy strategies by presenting cell surface antigens.

In some embodiments, the cancer immunotherapy utilizes and/or is linked to any of the other aspects described herein. For example, while immunotherapy is being implemented with the physical area network, gaming/videos are able to be utilized in conjunction as described herein. For example, the cancer decoys are implemented in a user's body, and a corresponding video game is implemented on a virtual reality headset, where the user plays by detecting cancer cells, deploying cancer decoys and/or using nano-nodes to attack the cancer cells.

In an exemplary cancer immunotherapy implementation, a physical area network includes a first set of nano-nodes encapsulated with a plasma-membrane derived from a cancer cell, and a second set of nano-nodes including a communication device and a plurality of chambers for containing different substances, such as inert substances when separate, but when mixed, the substances are activated and/or treat/kill the cancer. For example, a first chamber includes Adriamycin and a second chamber includes Cytoxan. Other examples of combinations of separate substances are Adriamycin and Taxotere; or Cytoxan, Methotrexate and Fluorouracil (with three separate chambers). Deriving the plasma-membrane from a cancer cell is able to be performed in any manner such as extracting the cancer cell from the user, processing the cancer cell including separating aspects of the cancer cell to obtain a "skin" or "shell" of the cancer cell which is able to be used as the coating. The coating is then placed on the nano-nodes in any manner such as placing the coating and the nano-nodes in a container and mixing the two to coat the nano-nodes. In another example, a cancer cell is isolated, the cancer cell is fractionated into one or more plasma membrane-derived vesicles, polymeric nano-nodes are synthesized and the plasma membrane-derived vesicle is fused with the nano-node. Further details on deriving the coating and applying the coating are able to be found in the U.S. Patent Application Publication No. 2018/0200194. The nano-nodes are able to be deployed in any manner such as by injection, inhalation, and/or ingestion. Any of the nano-nodes are able to include one or more chambers for storing items such as medications. Any of the nano-nodes are able to include sensor components. The nano-nodes are able to be positioned based on DNA methylation as described herein. The first set of nano-nodes and/or the second set of nano-nodes communicate with each other, additional nano-nodes, one or more nano-routers and/or one or more nano-micro interfaces. The nano-router is able to be used to trigger the first set of nano-nodes to activate an immune response against the cancer cell to treat the cancer. In some embodiments, the communicating nano-nodes and medication nano-nodes are separate sets of nano-nodes. The physical area network components are able to utilize encryption/decryption schemes, THz, communication, in vivo communication which accounts for the medium the communication is being sent through, and/or translation implementations. The nano-nodes, nano-routers and nano-micro interface are able to be used in conjunction to implement a gaming system corresponding to the cancer treatment as described herein. The nano-nodes are able to be stationary or mobile and move via magnetism, autonomously (e.g., based on sensors), random movement, flow and/or any other manner. Determining a size of a tumor or other medical issue is able to be based on surrounding the tumor or part of the tumor with nano-nodes which are capable of measuring distances between each nano-node as described herein, and based on the number of nano-nodes (and calculated distances), a size is able to be computed. The physical area network is able to communicate with a social network or other devices through the social network. The nano-nodes and/or nano-routes are able to include ID codes and/or family IDs. The information acquired by the physical area network is able to be processed and analyzed in any manner and for any purpose. Any other aspects described herein are able to be incorporated or used with the cancer immunotherapy implementation.

Figure 3:
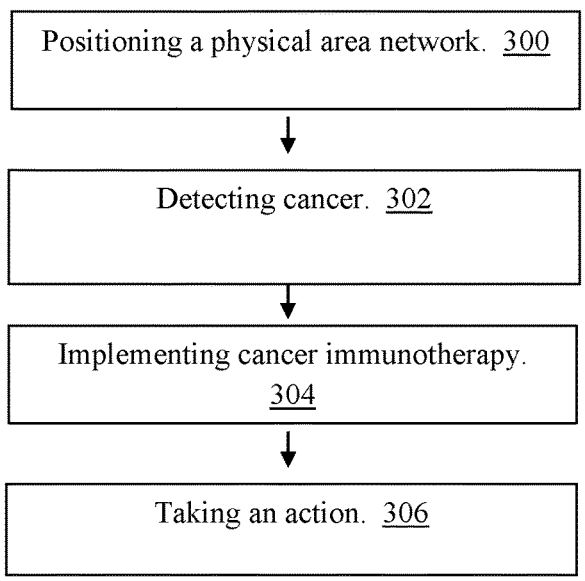
FIG. 3 illustrates a flowchart of a method of implementing cancer immunotherapy according to some embodiments.

FIG. 3 illustrates a flowchart of a method of implementing cancer immunotherapy according to some embodiments. In the step 300, the physical area network is positioned. For example, nano-nodes are injected, ingested, inhaled, and/or implanted. In the step 302, cancer (or another illness/issue) is detected. For example, DNA methylation detection is implemented. In another example, nano-nodes detect a mass based on mobility issues (e.g., nano-node is blocked or not moving). In another example, the nano-nodes are utilized with a medical imaging device. In the step 304, cancer immunotherapy (or another immunotherapy) is implemented as described herein. In some embodiments, the cancer immunotherapy includes utilizing decoys. In the step 306, an action is taken. The action taken is able to include one or more actions. For example, in addition to implementing immunotherapy, medication is delivered to the cancer by the nano-nodes. In another example, nano-nodes are used to measure the size of the cancer and communicate the information to the nano-micro interface and/or another device (e.g., doctor device). In another example, the nano-nodes communicate progress of the immunotherapy. In another example, as described herein, the nano-nodes communicate with the nano-micro interface which communicates with a gaming system/mobile device to implement a corresponding game/video. In some embodiments, fewer or additional steps are implemented. In some embodiments, the order of the steps is modified.

In an exemplary method, a method of treating cancer includes positioning a physical area network in a user and activating an immune response against the cancer cell in the user, thereby treating the cancer. The physical area network includes a first set of nano-nodes and a second set of nano-nodes. The surface of each nano-node in the first set of nano-nodes is encapsulated with one or more plasma membrane-associated components. The plasma membrane is derived from a cancer cell and a second set of nano-nodes. Each nano-node in the second set of nano-nodes includes a communication device to communicate with a nano-node, a nano-router and/or a nano-micro interface.

In another exemplary method, a method of disrupting cancer cell-stromal cell signaling in a user includes isolating a cancer cell from the user, administering to the user a composition including a nano-node, where the nano-node surface is encapsulated with one or more plasma membrane-associated components, and where the plasma membrane is derived from the cancer cell, thereby disrupting cancer cell-stromal cell signaling in the subject. In another example, the method includes isolating a cancer cell from the user, administering to the user a composition comprising a nano-node, wherein the nano-node surface is encapsulated with one or more plasma membrane-associated components, and where the plasma membrane is derived from the cancer cell, where the composition includes a detectable label and identifying the detectable label, thereby detecting a cancer cell-stromal cell interaction.

An exemplary method of preparing a composition including a nano-node, wherein the nano-node surface is encapsulated with one or more plasma membrane-associated components, and wherein the plasma membrane is derived from a cancer cell. The method includes: isolating a cancer cell, fractionating the cancer cell into one or more plasma membrane-derived vesicles; synthesizing polymeric nano-nodes; and fusing the plasma membrane-derived vesicle with the nano-node.

An exemplary composition includes a nano-node, wherein the nano-node surface is encapsulated with one or more plasma membrane-associated components, and where the plasma membrane is derived from a cancer cell.

Figure 4:
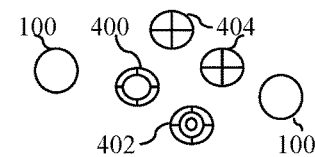
FIG. 4 illustrates a diagram of utilizing the physical area network to implement cancer immunotherapy according to some embodiments.

FIG. 4 illustrates a diagram of utilizing the physical area network to implement cancer immunotherapy according to some embodiments. Nano-node decoys 400 are able to be utilized in the cancer immunotherapy such as by attracting cancer cells 404. The nano-node decoys 400 are able to be nano-nodes with a cancer cell membrane and/or another types of cancer-coating. In some embodiments, the nano-node decoys 400 are able to include internal components as described herein such as power components, motion components, communication components and processing components. In some embodiments, the nano-node decoys 400 are more simplistic and do not include additional components. Medicated nano-node decoys 402 are able to be deployed which attract the cancer cells and also include medication (or another substance) which is able to harm or kill the cancer cells. Additional nano-nodes 100 are able to be utilized to monitor the situation for example, by detecting the number of cancer cells, determining a size of a mass and/or detecting any chemical/biological reactions related to the cancer. The nano-nodes 100 are able to take other actions such as: deploying medication, communicating with the nano-node decoys 400, and/or communicating with other nano-nodes 100, nano-routers 102 and/or the nano-micro interface 104 (e.g., progress or for gaming purposes).

In some embodiments, the one or more nano-nodes 100 are configured to detect methyl-CpG and/or DNA methylation.

In some embodiments, the nano-nodes 100 are able to detect biomarkers for specific cancers and/or circulating tumor DNA (ctDNA) for general cancer detection. For example, an abnormally high proportion of cfDNA from a specific tissue can indicate the possibility of a tumor in that tissue. "CancerLocator: non-invasive cancer diagnosis and tissue-of-origin using methylation profiles of cell-free DNA" by Kang, Shuli, et al., Genome Biology, 2017, describes the process of using methylation data to detect cancer.

Nano-nodes 100 are able to be used to detect biomarkers/ctDNA. In some embodiments, since the nano-nodes 100 are able to be positioned throughout a user's body, the nano-nodes 100 are able to be used to determine a location of the cancer, attach to the cancer, and/or attack/treat the cancer. For example, if nano-nodes 100 positioned in CSF detect the ctDNA before any other nano-nodes 100 detect the ctDNA, then the detection (including identification information/location information) is sent to the nano-micro 104 interface to indicate the location (e.g., brain) of the detection (e.g., possible cancer). The real-time detection of the cancer and the location of the cancer will dramatically increase how quickly a user is treated and thus survival rates.

By detecting methyl-CpG, DNA methylation and/or cancer biomarkers, instead of injecting nano-nodes to a specific/target location, the nano-nodes are able to move and locate the cancer. For example, the nano-nodes are ingested or injected into a user's bloodstream, and then based on detection and analysis, the nano-nodes navigate to a desired location such as a cancer site. For example, after the methyl-CpG or other markers are detected, the user undergoes additional medical imaging/testing. Then, based on the additional information, directional information is able to be sent to the nano-nodes for them to move. Furthering the example, a user uses the nano-micro interface to send cancer-location information, or the information is automatically sent from a medical device to the nano-nodes.

Methylation patterns/signatures of tumor cells are altered compared to those of normal cells. In some embodiments, the methylation patterns/signatures are detected using a nano-node 100 which is transmitted to the nano-micro interface 104. For example, small amounts of DNA are able to be captured. Once captured, DNA methylation may be monitored by restriction enzyme digestion or bisulfite conversion followed by amplification of the desired genomic region with the polymerase chain reaction. Methyl-binding protein or antibodies that bind specifically to methylated-CpG residues are able to be used to interrogate the status of "DNA methyome" of diseased tissue in an efficient manner. [Tsou et al., DNA methylation analysis: a powerful new tool for lung cancer diagnosis, Oncogene (2002) 21, 5450-561 and Qureshi et al., Utility of DNA methylation markers for diagnosing cancer, International Journal of Surgery 8 (2010) 194-198]

Pacific Biosciences has developed a real-time single molecule sequencing approach that is able to recognize methylated nucleotides from fluorescently labeled nucleotides present within a DNA strand. A change in the fluorescense pulse is represented by the DNA polymerase catalyzing the labeled nucleotides. Researchers from the University of Illinois have developed a technique to detect DNA methylation through the use of nanopore sensors. After a specific methyl-CpG nucleotide binding domain protein (MBD1) is applied to DNA, a vertical ionic current is generated to present across the nanopore. This method has been shown to avoid overlapping in the methylations pattern, ensuring accuracy and precision. [Cuffari, Benedette, Nanotechnology in 2017: The Story So Far, <www.azonnano.com/article.aspx?ArticleID=4443]

Medical Imaging

In some embodiments, the nano-nodes are positioned to assist in medical imaging (e.g., an ultrasound, CT scan, MRI, x-ray). For example, the nano-nodes are able to include materials/chemicals to help distinguish features while acquiring a medical image. Furthering the example, the nano-nodes are ingested to help outline a user's esophagus, stomach, intestines, liver, gall bladder, and/or other organs. Similarly, the nano-nodes are able to be inserted into the amniotic fluid to help with an ultrasound of a fetus. For example, the nano-node payload includes a metal ion, atom, or cluster, and then the nano-nodes are positioned in the user's body in any manner described herein. Medical imaging is then applied, and the metal of the nano-node is able to help display the outline of a tumor, a blockage in an artery, a hole/gap where there should not be one, and/or any other issue/feature.

Nanodiamonds are able to be used for medicine delivery and imaging. Nanodiamonds are approximately 5 nm in size comprising non-toxic materials whose exemplary surface area and related properties provide advantages for drug medicine delivery and imaging. Researchers from Athinoula A. Martinos Center for Biomedical Imaging at Massachussetts General Hospital have coated the surface of nanodiamonds with a paramagnetic gadolinium (III) agent to generate a complex which allows for conventional T1-weighted MRI imaging. By incorporating the nuclear Overhauser effect to the 13C nuclei which specifically targets and magnetically excites the nucleus to alter the equilibrium of the nanodiamond, the researchers were able to overcome maintaining hyperpolarization, and were able to allow for nanodiamond imaging to maintain its contrast for long-term biological imaging purposes. Nanodiamonds are very useful in tracking nanoparticle accumulation in certain biological regions such as the brain, lymph nodes and the liver. [Cuffari, Benedette, Nanotechnology in 2017: The Story So Far, <www.azonnano.com/article.aspx?ArticleID=4443>]

Figure 5:
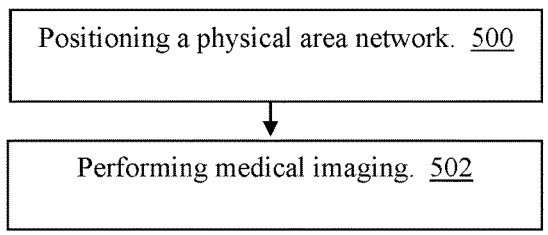
FIG. 5 illustrates a flowchart of a method of implementing medical imaging according to some embodiments.

FIG. 5 illustrates a flowchart of a method of implementing medical imaging according to some embodiments. In the step 500, a physical area network is positioned. As described herein, the nano-nodes and/or nano-routers are able to be positioned in any manner such as injection, ingestion, and so on. For medical imaging, the nano-nodes will be positioned or move to a desired location to assist in medical imaging. For example, the nano-nodes are injected into a patient's bloodstream using a syringe, and they travel to the patient's liver for medical imaging of the patient's liver. In some embodiments, the nano-nodes are able to inform a patient or other person (e.g., doctor, technician) that they are in place. For example, the nano-nodes determine their location and/or an accumulation of nano-nodes in a location, and inform the technician by communicating through the nano-micro interface, so that the technician knows when to begin the medical imaging. In the step 502, medical imaging is performed. For example, an MRI (or any other medical imaging technique) is performed, and the nano-nodes assist in the medical imaging by providing a clearer image or more distinct features. In some embodiments, fewer or additional steps are implemented. For example, in some embodiments, the nano-nodes are configured to actively move to a location to exit the patient (e.g., bladder) after a period of time or after receiving a signal that the test is over. In some embodiments, the order of the steps is modified.

Movement

ETH Zurich and Technion researchers have developed an elastic "nanoswimmer" polypyrrole nanowire about 15 micrometers long and 200 nm thick that is able to move through biological fluid at approximately 15 micrometers per second. The nanoswimmers are able to be used to deliver medication and magnetically controlled through the bloodstream. [Nanorobots: Where We Are Today and Why Their Future Has Amazing Potential, <https://singularityhub.com/2016/05/16/nanorobots-where-we-are-today-and-why-their-future-has-amazing-potential>

In some embodiments, the nano-nodes 100 include helical flagella for movement. In some embodiments, arms (similar to cilia) vibrate when receiving ultrasound or magnetic field from an external source and cause the nano-nodes 100 to move. In some embodiments, an external device provides ultrasonic signals to direct the nano-nodes 100 to a location. For example, the nano-micro interface 104 provides the signals. In some embodiments, the nano-nodes 100 include capacitors and utilize fluids to provide jet propulsion. The nano-nodes 100 and/or nano-routers 102 are able to move utilizing any implementation.

The nano-nodes 100 and/or the nano-routers 102 are able to travel (e.g., in a user's bloodstream, lymphatic system, digestive system) and/or are positioned in a specific location (e.g., ear, tooth, brain, foot, and/or any other body part). In some embodiments, the nano-nodes 100 and/or nano-routers 102 are movable using an external source (e.g., using a magnet, electromagnetic device). For example, a nano-node and/or nano-router includes nanoparticles of a magnetic material such as iron such that a magnet is able to attract the nano-nodes/nano-routers. In some embodiments, some nano-nodes and/or nano-routers include the attractive component (e.g., nanoparticles of iron) and some nano-nodes/nano-routers do not, so that only some of the nano-nodes or nano-routers move when desired (e.g., when a magnet is placed near the user's body or EM field is generated near the user's body). In some embodiments, some nano-nodes and/or nano-routers include a first material (e.g., nano-particles), and some nano-nodes/nano-routers include a second material (e.g., nano-particles), where the first material is attracted by a magnet and the second material is attracted by (or repelled by) something else such as water or heat (or the second material is not attracted by a magnet). In some embodiments, the nano-micro interface 104 (e.g., wearable clothing, watch, earrings, necklace) includes a magnetic or electromagnetic component capable of attracting the magnetic nano-nodes 100 and/or nano-routers 102. In some embodiments, the nano-micro interface 104 is able to activate the magnetic/electromagnetic component on demand, periodically (e.g., once every hour or at 7p), randomly and/or any other activation aspects.

In some embodiments, the one or more nano-nodes 100 and/or the one or more nano-routers 102 move around the body. In some embodiments, the one or more nano-nodes 100 and/or the one or more nano-routers 102 move autonomously. For example, the nano-nodes 100 or nano-routers 102 move in a continuous forward direction, move with or against the flow of bodily fluids (e.g., blood), and/or move within a specific body location/area (e.g., based on oxygen levels, salinity levels, tissue detection, magnetization, EM levels). With movement, the communication between the nano-nodes 100 and the one or more nano-routers 102 may be disrupted. There are several solutions to this issue. The nano-nodes 100 are able to communicate with each other to send information from one nano-node to other nano-nodes to reach a nano-router 102. For example, the fewest hops from a first nano-node to a nano-router is determined, and the nano-nodes each transmit the information from the first nano-node to the next until the information reaches the nano-router. Similarly, when communicating commands from the nano-micro interface 104 to the nano-nodes 100, the information is communicated from a nano-router 102 to nano-nodes until the information reaches the target nano-node.

In some embodiments, each nano-node and/or nano-router has a specific/designated body location. For example, a first group of nano-nodes and a nano-router are positioned in the small intestine, a second group of nano-nodes and a nano-router are positioned near the brain (e.g., in the cerebral spinal fluid), and a third group of nano-nodes and a nano-router are positioned in/near the heart.

Figure 6:
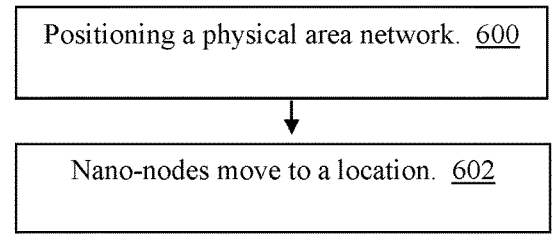
FIG. 6 illustrates a flowchart of movement of nano-nodes according to some embodiments.

FIG. 6 illustrates a flowchart of movement of nano-nodes according to some embodiments. In the step 600, the physical area network is positioned (e.g., nano-nodes are ingested, injected). In the step 602, the nano-nodes move to a desired location. In some embodiments, the nano-nodes move to a specific location and stay in that location (e.g., stay in the CBF). In some embodiments, the nano-nodes continuously move (e.g., in a user's blood stream). As described herein the nano-nodes are able to move as clusters or individually, and are able to move in any manner (e.g., via vibration, flagella, cilia, propulsion). In some embodiments, the nano-nodes move autonomously, by receiving a signal/instruction, by being pulled using an electromagnet and/or any other manner. Nano-routers are also able to move in the same or similar manners as the nano-nodes. In some embodiments, fewer or additional steps are implemented. In some embodiments, the order of the steps is modified.

Communication/Terahertz

The nano-nodes 100, nano-routers 102, nano-micro interface 104 and control unit 106 are able to communicate using any manner of communication. In some embodiments, each component uses the same form of communication, and in some embodiments, a variety of communication implementations are utilized. For example, nano-nodes communicate with other nano-nodes and nano-routers using a first implementation, but the nano-micro interface and the control unit utilize a second implementation. Some possible forms of communication include molecular communication and nano-electromagnetic communication.

Molecular communication involves transmitting and receiving information encoded in molecules. Nano-nodes encode information into information molecules (e.g., DNA, proteins, peptides). Information is able to be transmitted within a DNA component. Routing at a micro gateway in molecular nano networks is able to be query-based.

Nano-electromagnetic communication involves transmitting and receiving electromagnetic radiation from components based on nanomaterials.

In some embodiments, graphene-based nano antennas are utilized to send and receive information in the terahertz band. For example, the nano-nodes, nano-routers and/or nano-micro interfaces include graphene-based nano-antennas with graphene strips that are a few nano-meters to a few micrometers long and roughly 10 times that wide or vice versa (e.g., 10 nano-meters long and 1 nanometer wide, or 10 nanometers wide and 1 micrometer long) combined with semiconducting materials such as indium gallium arsenide. The graphene is a one atom thick sheet of bonded carbon atoms in a honeycomb crystal lattice. In some embodiments, the graphene is formed into nano-ribbons, rolled into carbon nanotubes or formed into bucky balls (graphene spheres). These graphene structures are able to be on the scale of less than 50 nm, including as small as 1 nm or smaller.

In some embodiments, the antenna is configured to communicate in the terahertz range (e.g., 0.1-10 THz and beyond up to optical frequencies). For example, plasmonic nano-antennas are utilized as described in Elayan, Hadeel, et al. In Vivo Communication in Wireless Body Area Networks. In some embodiments, the body is modeled as a collection of elements such as cells, organelles, proteins and others with different geometries, arrangements, electrical properties and optical properties.

In vivo communication is a signal transmission field which utilizes the human body as a transmission medium for electrical signals. Electrical current induction into the human tissue is enabled through transceivers. In some embodiments, the information is encoded and compressed before or during transmission. A transmitter transmits the information using a current-controlled coupler unit which couples/attaches to a user's body (e.g., veinous wall, muscle, internal organ, bone). The user's body acts as the transmission channel. Electrical signals travel into/through the human tissue. A receiver (e.g., an analog detector) receives the signal traveling through the tissue. In some embodiments, the receiver (on another nano-node 100 or a nano-router 102) amplifies the induced signal. In some embodiments, the nano-node 100 or the nano-router 102 converts the signal to a digital signal (e.g., using A/D converter) and performs data demodulation, decoding and/or extracting. In the in vivo channel, the electromagnetic wave passes through various dissimilar media that have different electrical properties. [Elayan, Hadeel, et al., In Vivo Communications in Wireless Body Area Networks]

In some embodiments, the dissimilar media is accounted for when communicating. For example, when communicating through fat, a signal is amplified or uses more power, than compared to communicating through bone, or vice versa. In some embodiments, based on the medium (e.g., blood, fat, bone, muscle, tendon), the frequency used for communication is modified (e.g., lower frequency for fat than for bone, or vice versa). In some embodiments, nano-nodes are designed to vary their frequency, and in some embodiments, different types of nano-nodes are generated (e.g., first set of nano-nodes communicates at a very high frequency, a second set of nano-nodes communicates at a high frequency, and a third set of nano-nodes communicates at a low frequency), and depending on the medium to communicate through, the appropriate nano-node is utilized to communicate. For example, a nano-node designed to communicate through blood acquires/receives information (e.g., from a sensor node) and communicates the information to a nano-node designed to communicate through bone which communicates the information to a nano-node designed to communicate through skin to a nano-router or a nano-micro interface.

Any communication implementation is able to be utilized (e.g., WLAN, Bluetooth, Zig-bee, RFID)

Any type of antenna is able to be used (e.g., monopole, dipole, in vivo, ex vivo, MIMO in vivo, SISO). As described herein, the nano-nodes 100 and/or nano-routers 102 (with the antennas) are able to be positioned anywhere in the body which may affect signal strength/capacity. In some embodiments, the nano-nodes 100 or nano-routers 102 are able to move (continuously) to find the best signal strength. In some embodiments, the distance between the nano-nodes 100 and/or nano-routers 102 is maintained or kept below a threshold (e.g., 10 µm, 10 mm, 10 cm) to ensure adequate signal strength. In some embodiments, instead of or in addition to distance, the signal strength is monitored to ensure adequate signal strength. For example, in some parts of the body, a distance of 10 cm may be too much, so based on a detected weak signal, the nano-nodes 100 maintain a shorter distance. In some embodiments, the distance threshold is set after taking initial readings (e.g., of signal strength), and then the distance threshold is used for maintaining distance. Distance measuring is able to be performed by any distance measuring method such as sending a signal and tracking time for detection or a response or a reflection. Signal strength measuring is able to be performed in any manner. Specific nano-nodes are able to be used for sensing/ detecting/measuring signal strength. The distance threshold may be based on medium (e.g., bone, blood). For example, a circuit on a nano-node 100, nano-router 102, or nano-micro interface 104 is configured to measure an amount of power a received signal has (e.g., how strong the signal is). In some embodiments, the nan-nodes and/or nano-routers move in a direction that makes the signal stronger by taking readings and comparing the successive readings and, if necessary/desired, go in that direction, until the signal is above the threshold (or above a second threshold which is higher than the minimum threshold).

In some embodiments, a subset of nano-nodes are dumb nodes capable of limited operation such as receiving a signal and transmitting the signal. For example, the subset of dumb nano-nodes do not have sensors or other specified elements/ components, and are able to perform limited tasks such as receiving a signal and forwarding/transmitting the signal to a next nano-node (smart or dumb) or a nano-router (which could also be smart or dumb).

In some embodiments, nano-node communication includes broadcasting information so that the information is able to reach multiple nano-nodes. For example, nano-node 1 broadcasts information which is received by nano-nodes 2, 3 and 4; and nano-nodes 2, 3 and 4 each broadcast the information, where the broadcast from nano-node 2 does not reach any other nano-nodes, the broadcast from nano-node 3 reaches nano-node 5, and the broadcast from nano-node 4 reaches nano-node 6 and nano-router 1, where nano-router 1 is able to broadcast/transmit the information to the nano-micro interface, and the information has made it outside of the body. In some embodiments, the number of hops is known or determined by the nano-nodes or another component, and only the nano-nodes/nano-routers with the shortest path continue to broadcast the information.

In some embodiments, nano-nodes are given a specified lifespan, to minimize the number of unsuspected, dead nano-nodes. In some embodiments, the nano-nodes periodically communicate an "alive" signal. In some embodiments, each nano-node periodically communicates an ID number, and a database (on the nano-micro interface or an external device such as a server) tracks nano-node IDs, and if a nano-node does not communicate its ID within a specified amount of time (e.g., before threshold), the nano-node is considered dead. The alive/dead information is able to be used in any manner such as determining when additional nano-nodes are needed to be added to the user.

In some embodiments, the one or more nano-routers 102 have more computational power than the one or more nano-nodes 100. The one or more nano-routers 102 collect information from the one or more nano-nodes 100, and transmit the information to the one or more nano-micro interfaces 104. The one or more nano-routers 102 are able to transmit control information to the nano-nodes 100.

In some embodiments, the nano-node broadcasts information upon acquiring the information for a period of time, and neighboring nano-nodes and/or nano-routers receive the information. Each nano-node broadcasts the received information until the information reaches a nano-router.

The nano-micro interface 104 receives data from the nano-nodes and/or nano-routers and transmits data to the nano-nodes and/or nano-routers. In some embodiments, a wearable device such as a smart watch includes/is the nano-micro interface 104. The nano-micro interface 104 includes a nano-communication component (e.g., antenna/ receiver) to communicate (nano-communications) with the nano-nodes 100 and/or the nano-routers 102, a translation component to translate the nano-communications (e.g., THz) to micro-communications (e.g., ZigBee) to send to the control unit 106 and/or external devices using a micro-communication component. In some embodiments, the translation is from a first language (e.g., first computer language) or protocol to a second language (e.g., second computer language) or protocol. In some embodiments, there is no translation, but the nano-micro interface 104 includes a nano-communication component to communicate with the nano-nodes and/or nano/routers and a micro-communication component to communicate with the control unit 106 and/or other external devices.

In some embodiments, the translation component is used to prevent hacking of the nano-nodes/nano-routers. For example, nano communications are not able to be sent from outside the body other than through the nano-micro interface 104. In a related example, the nano-micro interface includes shielding (e.g., inside a watch is a plate with the communication unit on the side of the plate closer to the user's body) such that any signals are sent specifically to the body to prevent unwanted receipt of the signal. Furthermore, the nano-micro interface encrypts the signal and/or uses a passcode such that only the nano-nodes and/or nano-routers are able to receive/decrypt the signal. Similarly, the nano-nodes and/or nano-routers only receive communications if the appropriate encryption and/or passcode is utilized/received. In another example, when a nano-node receives a communication, the nano-node sends a low-powered ACK, and if the nano-node receiving the ACK did not send the original communication, then that nano-node sends another communication to the originally receiving nano-node to ignore the previously received communication. In another example, the nano-nodes and/or nano-routers use a different communication mechanism than external devices, where the nano-micro interface 104 is capable of communicating with the nano-nodes/nano-routers. In some embodiments, there is a designated internal communication point (e.g., 1 nano-router) which communicates with a designated external communication point (e.g., nano-micro interface), and their communication functionality is dependent upon close proximity (e.g., must be within a distance threshold such as 1-5 cm). The nano-router then communicates the information throughout the internal physical area network. For example, the nano-micro interface and the nano-router send communications with time stamps, and if the time stamp indicates the communication took too long (indicating it traveled a longer distance than allowed), then the communication is rejected/ignored. This prevents foreign devices from communicating with the nano-nodes/nano-routers.

In some embodiments, a multi-channel wireless network is utilized to enable multiple nodes to transmit data simultaneously using the different channels. For example, instead of one nano-node acquiring data and/or sensing information, multiple nano-nodes acquire the data and communicate the data on different channels either to additional nano-nodes which pass the data on, or the nano-nodes communicate directly with one or more nano-routers which pass the data on, or the nano-nodes communicate directly with a nano-micro interface which has multiple channels to receive the data simultaneously. Any of the components of the physical area network are able to include multi-channel capabilities to send and/or receive multiple pieces of data simultaneously. For example, 8 nano-node sensors (located near each other or in a cluster) are used to detect various chemical/blood markers including location information. Each of the 8 nano-node sensors send some of the information detected (e.g., a first sensor sends salinity levels on a first channel, a second sensor sends blood sugar levels on a second channel, a third nano-node sends location information on a third channel, a fourth nano-node sends heart rate information on a fourth channel and so on). The information is sent to a nano-router with multi-channel capabilities (or to many nano-routers with or without multi-channel capabilities) which then forwards the information to a nano-micro interface with multi-channel capabilities, so that the information is received at approximately the same time for processing, analysis and output.

In some embodiments, communication is implemented using binary decoders utilizing multiple wires. In some embodiments, one or more wires are utilized but a voltage amount is varied to provide the communication.

In some embodiments, the components of the physical area network are synchronized. The components are able to be synchronized in any manner and are able to be synchronized for any purpose. For example, the nano-nodes and/or nano-routers are able to perform a clock check with the nano-micro interface to ensure the clocks are synchronized. The nano-nodes are able to be synchronized in terms of movement so that the nano-nodes are properly distributed throughout the body. For example, periodically or randomly, the nano-nodes and/or nano-routers send out a location signal to inform other components where they are. As described herein, the nano-micro interface is able to store a map of the nano-nodes and/or nano-routers, and by plotting where the nano-nodes are located, the nano-micro interface is able to ensure the nano-nodes are properly positioned. In some embodiments, the strength/weakness of a signal is used to determine the location of the nano-nodes. In some embodiments, the physical area network components are synchronized in communication.

In some embodiments, reliable transport protocol or a similar protocol is implemented.

Data authentication is utilized to authenticate a sender of data and validate the integrity of the data. As described herein, DNA information is able to be utilized to authenticate the data by sending/receiving information of a DNA segment and verifying the DNA segment.

In some embodiments, a coding/communication scheme is utilized such as Spread in Time On-Off Keying (TS-OOK) protocol where communication data is sent using a sequence of pulses interleaved by a constant duration randomly selected.

In some embodiments, as the nano-micro interface receives information from the nano-nodes and/or nano-routers, the nano-micro interface is able to communicate the information and/or an alert to a remote contact (e.g., doctor, hospital, police, firemen, a relative). For example, if the nano-nodes, nano-routers, and/or nano-micro interfaces detect a arterial blockage, a viral/bacterial infection, stroke, high blood pressure, an elevated temperature, a heart arrhythmia, and/or any other illness/situation, an alert is sent via wireless, telephone, satellite, SMS, email, tweet, and/or any other form of communication/medium of communication to the remote contact. In some embodiments, multiple communications occur simultaneously to the same or different contacts. For example, a 911 phone call is made to send police, fire and an ambulance, and the recorded medical information (e.g., detection of an arrhythmia) is sent to the ambulance/first responder device and/or a hospital device.

Figure 7:
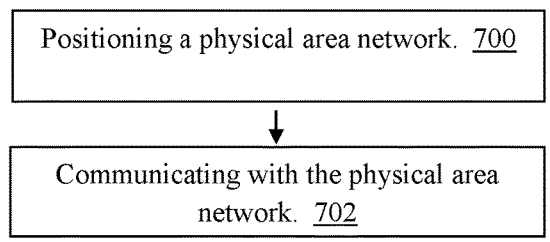
FIG. 7 illustrates a flowchart of a method of a physical area network communicating according to some embodiments.

FIG. 7 illustrates a flowchart of a method of a physical area network communicating according to some embodiments. In the step 700, a physical area network is positioned. In the step 702, the physical area network components (e.g., nano-nodes, nano-routers, nano-micro interface and more) communicate. As described herein, there are a variety of ways of communicating—THz communication, in vivo communication, accounting for differences in materials, determining shortest paths, and more. In some embodiments, nano-nodes communicate with nano-nodes and/or nano-routers. In some embodiments, nano-micro interfaces communicate only with nano-routers or nano-routers and nano-nodes. The physical area network is able to communicate with external devices as well (depending on the implementation and/or device). In some embodiments, communications are encrypted and otherwise protected. In some embodiments, fewer or additional steps are implemented. In some embodiments, the order of the steps is modified.

Encryption

In some embodiments, information is encrypted before it is communicated. In some embodiments, information within the body (e.g., from nano-node to nano-node or nano-router) is not encrypted, but information sent from within the body to outside the body (e.g., from nano-node or nano-router to nano-micro interface) is encrypted. Any type of encryption is able to be utilized. In some embodiments, the encryption implementation is DNA encryption. Any forms of DNA encryption are possible. For example, a nano-node is able to collect DNA information while inside the human body, and then use the DNA information (or a segment of the DNA information) as a key for encryption. Another device such as a nano-micro interface or a server also includes DNA information from the specific user and uses that information for decryption. Furthering the example, a communication sent from a nano-node is encrypted using a key based on acquired DNA information, and when the communication reaches the nano-micro interface, the communication is decrypted using DNA information stored in the nano-micro interface or another device. By utilizing DNA information for encryption, any snooping devices will not be able to decrypt the encrypted communication thus keeping the health information (or other information) safe. In another example, the segment of the DNA information used for encryption continuously or randomly changes further protect the communications. Furthering the example, the nano-node (or nano-router) and the nano-micro interface have a table of the appropriate segment used for encryption/decryption. For example, the nano-node indicates that segment 83 of the user's DNA was used for encryption, so the nano-micro interface searches using a table for segment 83 for decryption. In some embodiments, the communications within the body are not encrypted, and only communications from within the body to outside the body (e.g., nano-router to nano-micro interface) are encrypted. Any encryption scheme is able to be utilized such as Triple Data Encryption Standard (DES), RSA encryption, Advanced Encryption Standard (AES), Twofish, and/or Blowfish.

Figure 8:
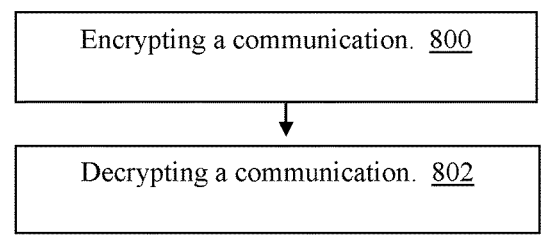
FIG. 8 illustrates a flowchart of a method of encryption utilized by the physical area network according to some embodiments.

FIG. 8 illustrates a flowchart of a method of encryption utilized by the physical area network according to some embodiments. In the step 800, a communication is encrypted. As described herein any form/type of encryption is able to be implemented such as DNA encryption. In the step 802, the communication is decrypted. The corresponding decryption is used. In some embodiments, fewer or additional steps are implemented. In some embodiments, the order of the steps is modified.

Power

As described herein, the nano-nodes and/or nano-routers are able to be powered using any power source such as an onboard battery or by harvesting energy from the environment such as hydroelectric power generation using blood flow, or ion power using chemicals within the body. In some embodiments, nano-nodes near the heart are able to acquire energy and/or charge an onboard battery using electrical pulses from the heart. The nano-nodes and/or nano-routers are able to include additional or other sources of power such as: temperature, light, fluid flow, muscle contractions, kinetic body movement, acid/battery, electrolytes (in blood) as battery, body heat, internal battery which receives charge from external source, external source using waves, microwaves, ultrasonic, magnetic fields to charge, and/or a piezo-electric membrane. Zinc oxide nanowires are able to be used for vibrational energy harvesting systems in nano-devices—the high density array of nanowires is used in piezo electric nano-generators. For example, a nanogenerator is able to harness mechanical energy from pulsing blood vessels and generate electricity to power a nano-node/nano-router.

In some embodiments, the nano-nodes and/or nano-routers are charged using conductive wireless charging. For example, the user's nano-micro interface is able to emanate a charge into the user's body which charges the nano-nodes. In some embodiments, the nano-nodes upon detecting low power travel to a specific location (e.g., wrist with the user's smart watch), and then communicate that they are in position to be charged which causes the nano-micro interface to charge the nano-nodes and/or nano routers. In another example, smart clothing is able to charge nano-nodes throughout the user's body.

Figure 9:
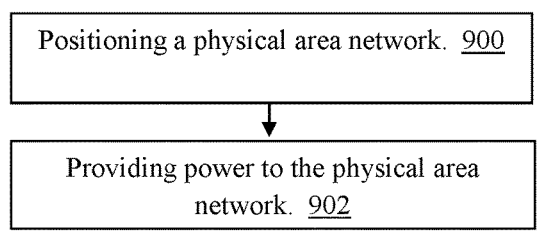
FIG. 9 illustrates a flowchart of powering the physical area network according to some embodiments.

FIG. 9 illustrates a flowchart of powering the physical area network according to some embodiments. In the step 900, the physical area network is positioned. In the step 902, power is provided to the physical area network. Providing power is able to be performed in any manner such as an onboard battery of a nano-node and/or nano-router. As described herein, in some embodiments, power is provided using kinetic energy, electrical energy from body parts such as the heart, fluid motion (e.g., blood stream), chemical energy from within the body and/or other method. In some embodiments, fewer or additional steps are implemented. In some embodiments, the order of the steps is modified.

Electronic Tattoos

Electronic tattoos 108 are able to be implemented in any manner such as thin, flexible patches containing flexible electrical components. The electronic tattoos 108 are able to be made of silicone, rubber, metal, carbon nanotubes, graphene, biomaterial, and/or any other appropriate material. For example, nanometer or micrometer silicon wired coils are embedded in rubber patches to connect one or more embedded sensors, antenna and/or any other components. In some embodiments, the electronic tattoos 108 are affixed to the outer surface of the skin, and in some embodiments, they are capable of being implanted in/under the skin. The electronic tattoos 108 are able to acquire vital signs and brain activity, monitor/stimulate muscle activity, perform blood tests, provide medication, communicate, and/or perform any other feature described herein. The electronic tattoos 108 able to communicate with nano-nodes 100, nano-routers 102, the nano-micro interface 104 and/or any other device, depending on the information. For example, the nano-nodes 100 send communications to each other and the nano-routers 102, and the nano-routers 102 communicate with the electronic tattoos 108, and the electronic tattoos 108 communicate with the nano-micro interface 104. In some embodiments, the electronic tattoos 108 are a type of nano-micro interface 104.

Analysis

Analysis of the collected body information determines the course of action (if any) to take. Analysis is able to take place within the physical area network or at another location. For example, the nano-micro interface performs analysis, and then based on that analysis the physical area network takes action. In another example, an offsite server receives data from the physical area network and processes the information including analyzing the information. As described herein, there are many ways of performing analysis of the acquired data.

Output/Effects

The output, effect or course of action taken are wide-ranging depending on the implementation. For example, medicine is deployed, a doctor is contacted, health conditions are monitored, additional nano-nodes are deployed, further analysis is performed, and or any other effect is implemented. The output/effects may vary depending on the implementation/application. As described herein, there are many types output, effect or actions that can be taken.

Figure 10:
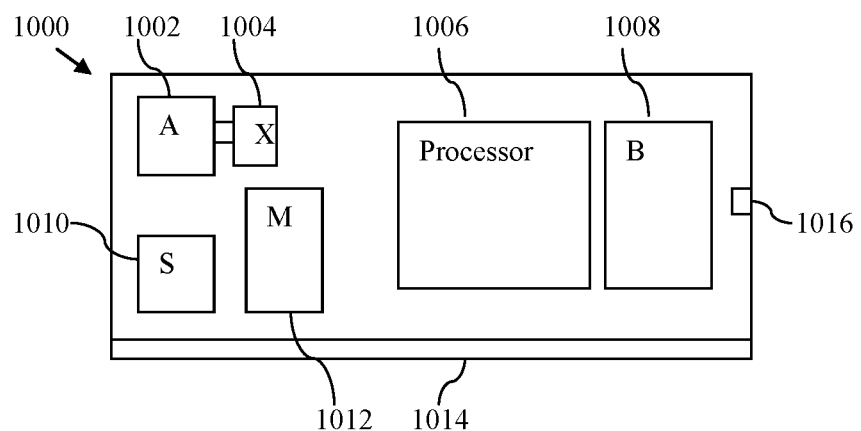
FIG. 10 illustrates a diagram of a nano-chip according to some embodiments.

FIG. 10 illustrates a diagram of a nano-chip according to some embodiments. The nano-chip 1000 includes one or more nano-antennas 1002, one or more nano-transceivers 1004 (e.g., EM transceivers), one or more nano-processors 1006, one or more nano-batteries 1008, one or more nanosensors 1010, one or more nano-memories 1012, one or more nano-power units 1014 and/or one or more couplers 1016.

As described herein, the nano-antenna 1002 and the nano-transceiver 1004 are used to communicate with other nano-devices. The nano-processor 1006 processes any data acquired by the nano-sensor 1010. The nano-sensor 1010 is described further herein and is used to acquire data such as by detecting chemicals, measuring electrical information, and/or measuring pressure amounts. The nano-battery 1008 is used to store energy to power the other components. The nano-memory 1012 stores instructions and/or acquired data. The nano-power unit 1014 are used to power the other components. For example, the nano-power unit 1014 includes zinc oxide nanowires which are used to harvest vibrational energy. The nano-power unit 1014 is able to implement any other type of energy nano-harvesting implementation such as a kinetic energy harvester, a propeller/windmill-type harvester. The dimensions of the nano-chip 1000 are able to vary for example: 1-10 µm×1-10 µm×1-10 µm, or 100 nm×100 nm×100 nm (or bigger or smaller such as 10 nm) depending on the implementation.

The nano-processor 1006 is able to use 32 nm, 20 nm or smaller transistor technology (e.g., 1 nm). In some embodiments, a graphene nanoribbon transistor is utilized (1 atom by 10 atoms=1 nm). The operating frequency is approximately 1 THz.

The nano-memory 1012 is able to be any memory such as gold nano-memory.

In some embodiments, the nano-chip is a nanomaterial-based design, and in some embodiments, the nano-chip is a biomaterial-based design. In some embodiments, the nano-chip 1000 includes fewer or additional components. For example, in some embodiments, the nano-chip 1000 does not include a battery 1008, and in some embodiments, the nano-chip 1000 does not include a nano-power unit.

The nano-antenna 1002 and nano-transceiver 1004 are able to be any antenna/transceiver; for example, the nano-antenna/nano-transceiver described in U.S. Pat. Nos. 9,397,758 and 9,643,841 to J. M. Jornet and I. F. Akyildiz.

The coupler 1016 is able couple to a user's body (e.g., veinous wall, bone, internal skin, tendon, fat) to send/receive messages using the user's body. For example, the coupler 1016 is able to be a hooking or clipping mechanism.

The various components are able to be coupled together using any connections such as carbon nanotubes and/or graphene ribbons.

Figure 11:
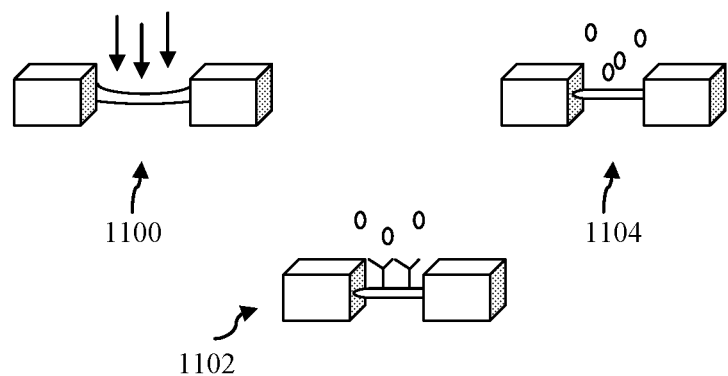
FIG. 11 illustrates diagrams of nano-sensing units according to some embodiments.

FIG. 11 illustrates diagrams of nano-sensing units according to some embodiments. A physical nanosensor 1100 is able to include a piezoelectric sensor. For example, the sensor is configured to measure changes in pressure, acceleration, strain, force or temperature by converting the detected information into an electric charge which triggers sending a signal. Furthering the example, carbon nanotubes or graphene are able to be configured in a manner to detect pressure/strain. In another example, zinc-oxide nanowires are able to be twisted, bent, squeezed to produce electricity which then causes a signal to be sent. For example, two ends of a zinc-oxide nanowire are connected to electrodes, and when the nanowire bends, the stretched outer side of the bent wire becomes positively charged, and the compressed inner surface becomes negatively charged.

A chemical nanosensor 1102 is able to be implemented by applying specified substances (e.g., palladium, zinc oxide, graphene, gold) to a base such as graphene or carbon nanotubes. In another example of a chemical nanosensor 1102, a nanocantilever oscillates at a resonant frequency, and when a chemical attaches to the cantilever, the oscillation stops which triggers a detection signal. A biological nanosensor 1104 is able to be implemented in a similar manner as the chemical nanosensor 1102 to detect biological molecules such as viruses by coating the cantilever with antibodies that capture a particular virus, and when a virus particle attaches to the antibody, the resonance frequency of the cantilever changes or the oscillation stops, which triggers a signal.

An electrochemical nanosensor is able to be implemented based on detecting change of resistance in a nanomaterial upon binding with an analyte, based on changes in scattering or the depletion or accumulation of charge carriers such as by using carbon nanotubes, conductive polymers or metal oxide nanowires as gates in field-effect transistors. Other potential sensors include, but are not limited to, electromagnetic or plasmonic nanosensors, spectroscopic nanosensors, magnetoelectronic or spintronic nanosensors and mechanical sensors.

Figure 12:
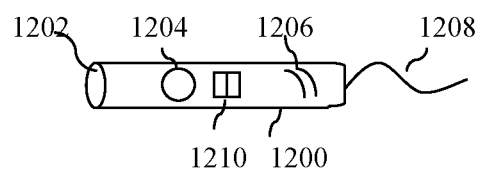
FIG. 12 illustrates a diagram of a mobile nano-node according to some embodiments.

FIG. 12 illustrates a diagram of a mobile nano-node according to some embodiments. The mobile nano-node 1200 is able to include a nano-camera 1202 (or micro-camera), a payload 1204 (e.g., a medication, magnetic component), a capacitor 1206, and a tail 1208. In some embodiments, the payload 1204 is stored in separate chambers/compartments (e.g., 2 or more chambers). In some embodiments, the payload 1204 includes a magnetic component to enable the nano-node to be attracted to an external magnetic source/device. In some embodiments, the payload 1204 is the medication, and the magnetic component is a separate component of the mobile nano-node 1200. The nano-camera 1202 is for taking pictures and/or video. In some embodiments, instead of or in addition to the payload 1204, tools such as a laser, knife, microwaves, ultrasonic signals, and/or other tools are included. For example at the tip or on the sides of the mobile nano-node 1200 is a sharp edge to cut. The capacitor 1206 is for providing power to the nano-camera 1202 and/or the tail 1208 which is for moving the mobile nano-node 1200. Additional components are able to be included such as a communication component/memory/processor 1210. Although one tail is shown, the propulsion mechanism is able to be two or more tails, a propeller, and/or any other propulsion mechanism. The communication component is able to be an antenna/transmitter/receiver. The mobile nano-node 1200 communicates the images/videos acquired to other nano-nodes 1200 (or nano-nodes 100), nano-routers 102, and/or the nano-micro interface 104. The nano-nodes 100 are able to be the mobile nano-node 1200 and/or any other nano-node. In some embodiments, the nano-nodes 100 and/or the mobile nano-nodes 1200 are able to swarm an area.

Figure 13:
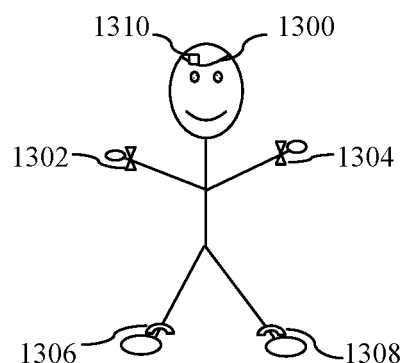
FIG. 13 illustrates a diagram of utilizing multiple nano-micro interfaces according to some embodiments.

FIG. 13 illustrates a diagram of utilizing multiple nano-micro interfaces according to some embodiments. For example, a headband nano-micro interface 1300 is worn on the head, watch or wristband nano-micro interfaces 1302, 1304 are worn on the wrists, and ankle nano-micro interfaces 1306, 1308 are worn around the ankles or in shoes. The nano-micro interfaces are able to be worn anywhere, and the number of nano-micro interfaces is able to be any number. The nano-micro interfaces are able to be equipped with a variety of components 1310 including, but not limited to, any computing components as well as magnetic components configured for attracting the nano-nodes and/or nano-routers. For example, by positioning the nano-micro interfaces on different locations of the body, by triggering one or more of the nano-micro interfaces, the nano-nodes are able to be attracted to a specific location of the body.

Security and Privacy

Security and privacy of the information acquired by the nano-nodes 100 is important. As described herein, the information is able to be anonymized. Additionally, any number of steps are able to be implemented to keep the information secure.

In some embodiments, the information from the nano-nodes 100 is only transmitted at specified times (e.g., at midnight) or during specified events (e.g., when heart rate is above a threshold, or when a specified device such as a nano-micro interface 104 is worn and detected). In some embodiments, the nano-nodes 100 and nano-routers 102 only communicate with confirmed devices such as the nano-micro interface 104 (e.g., watch). The devices are able to be confirmed by sending a specialized password or key which confirms the nano-micro interface 104 as an appropriate device (or another sync process).

In some embodiments, encryption is employed to ensure the information is not snooped or otherwise improperly acquired. For example, a nano-router 102 or an internally placed nano-micro interface 104 includes an encryption mechanism which encrypts any information acquired by the nano-nodes 100. Another device (e.g., watch, server, or doctor's device) includes a decryption mechanism. Any form of private key/public key encryption is able to be implemented.

To ensure uncorrupted data, any type of error detection and correction is able to be implemented.

Any other type of encryption/security/privacy is able to be implemented such as those described in A. Lounis, A. Hadjidj, A. Bouabdallah, and Y. Challal, "Healing on the cloud: secure cloud architecture for medical wireless sensor networks," Future Generation Computer Systems, vol. 55, pp. 266-277, 2016; B. Bezawada, A. X. Liu, B. Jayaraman, A. L. Wang, and R. Li, "Privacy Preserving String Matching for Cloud Computing," in Proceedings of the 35th IEEE International Conference on Distributed Computing Systems, ICDCS '15, pp. 609-618, July 2015; and S. Chandrasekhar, A. Ibrahim, and M. Singhal, "A novel access control protocol using proxy signatures for cloud-based health information exchange," Computers & Security, vol. 67, pp. 73-88, 2017.

Implementations

In some embodiments, a parent-child structure is utilized for the nano-nodes 100 and/or nano-routers 102. For example, some of the nano-nodes 100 are parent nodes which receive communications from the children nodes.

In some embodiments, a nano-node 100 sends out a signal and waits for an acknowledgment (ACK) signal back from another nano-node 100, nano-router 102 or nano-micro interface 104. Once the ACK is received, the nano-node 100 sends any acquired data (e.g., sensor results). In some embodiments, if the nano-node 100 does not receive an ACK within a specified time period, the nano-node 100 either pauses for a specified amount of time or moves, and then re-tries sending a signal.

In some embodiments, one or more nano-nodes 100 move periodically within a designated area (or freely), so that they may detect a signal sent from another nano-node, and once a signal is detected, the nano-node stops, sends an ACK, and waits to receive the data from the other nano-node.

In some embodiments, one or more nano-nodes 100 transmit distance information and/or location information. For example, the distance information includes how many hops from the nano-node to other nano-nodes, nano-routers, and/or nano-micro interfaces. In some embodiments, each nano-node 100 is given a location specific identifier (e.g., ID=1 means it is located near the brain, ID=2 means the node is located near the heart, and so on). In some embodiments, the nano-nodes 100 are able to sense their location based on body fluid detection/analysis and relay the location information. In some embodiments, an external device is able to provide a signal or trigger location information of the nano-nodes 100. For example, a nano-micro interface 104 or another device is able to be toggled to the current location (e.g., user toggles to heart, when placing on chest near heart), which signals to the nano-nodes near the heart a specific ID for the heart.

By using the path with the shortest number of hops, the nano-nodes 100 are able to save energy, and the communication process is optimized. Once a path is determined, that path is able to be saved. However, if any of the nano-nodes 100 of the path move, the distances/hops are re-calculated. Time Division Multiple Access (TDMA) is able to be implemented for scheduling between nodes.

In some embodiments, the nano-nodes 100 are able to go into low-power mode, sleep mode, idle mode, or any other power-saving mode. The nano-nodes 100 are able to be awoken by receiving a signal from the nano-micro interface 104.

In some embodiments, the nano-nodes 100 have different data rates. For example, some nano-nodes 100 have higher data rates than other nano-nodes 100, and the nano-nodes 100 are able to be positioned and utilized based on their data rates.

There are many other implementations possible such as those described by Seo et al., Quwaider et al., Watteyne et al., Nabi et al., Guo et al., Tsouri et al., and Javaid et al. as mentioned in Sharma, Neelam et al. "An Enhanced-Simple Protocol for Wireless Body Area Networks," Journal of Engineering Science and Technology, Vol. 13, No. 1 (2018).

Applications

As described herein, the physical area network is able to be used in any application such as brain cell monitoring, blood sugar monitoring, heart monitoring, cancer monitoring, targeted drug delivery, illness monitoring, and/or any other application.

In some embodiments, one or more nano-nodes, nano-routers, and/or nano-micro interfaces are embedded in, implanted on and/or otherwise attached to a tooth and/or filling. In some embodiments, the jaw movement is able to be used for power. For example, the embedded device includes an inertial component configured for generating power from kinetic energy. In another example, the saliva is able to be used as a power source such as the movement of the saliva is able to be used to generate hydroelectric power. In some embodiments, the embedded device is able to be used to analyze DNA. In another example, the embedded device includes a sensor to detect one or more specified enzymes/proteins/allergens such as gluten or lactose. Upon detection, the embedded device communicates the information and/or triggers an alert. For example, the embedded device is a nano-node configured to detect gluten, and upon detection, the nano-node sends a signal to a nano-micro interface (e.g., watch) to blink and/or beep to alert the user.

Figure 14:
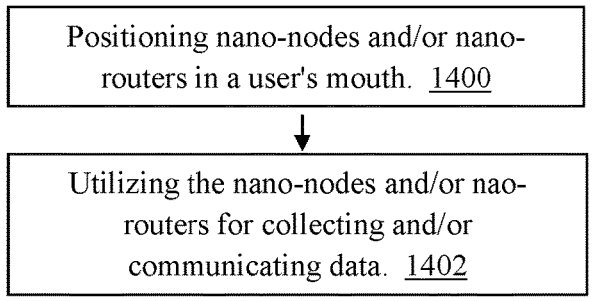
FIG. 14 illustrates a flowchart of a method of utilizing nano-nodes positioned in a user's mouth according to some embodiments.

FIG. 14 illustrates a flowchart of a method of utilizing nano-nodes positioned in a user's mouth according to some embodiments. In the step 1400, one or more nano-nodes and/or nano-routers are positioned in a user's mouth (e.g., affixed to or embedded in a user's tooth). For example, a filling includes a nano-node and/or a nano-router. In the step 1402, the nano-nodes and/or nano-routers collect and/or communicate data. For example, nano-nodes are able to detect saliva levels, food allergens, and/or other substances. Furthering the example, a nano-node detects the presence of a peanut allergen in a food item, and sends a signal to alert the user (e.g., alarm on smart phone or watch). In another example, a nano-router is used as a communication point where the filling is able to act as an antenna or an amplifier. The nano-router on the filling is able to be used as the main communication point between internal nano-nodes and the nano-micro interface. In some embodiments, fewer or additional steps are implemented. In some embodiments, the order of the steps is modified.

In some embodiments, each nano-node and/or nano-router includes an identification (ID) code/number. One or more devices within the physical area network includes a mapping of the nano-nodes (including their IDs), including distances between each nano-node and each nano-router. For example, the distance from nano-node 1 to nano-node 2 to nano-router 1 is 5 cm, and the distance from nano-node 1 to nano-node 3 to nano-router 1 is 4 cm, so the route through nano-node 3 is used, since it is shorter. In some embodiments, if it is determined that a nano-node or nano-router is too far (e.g., exceeds a distance threshold—over 10 cm—from the nearest nano-node or nano-router), then the nano-node moves (e.g., is sent a command to move closer to another nano-node, or moves until it is under the threshold). In some embodiments, the nano-nodes (or nano-routers)

continuously determine the distance to their nearest nano-node, and if the distance exceeds a threshold, the nano-node moves until the distance is less than the threshold. In some embodiments, nano-nodes and/or nano-routers move as a chain or a group. For example, if the distances between nano-node 4 and nano-node 5 is above a threshold, then nano-nodes 1, 2, 3 and 4 move towards nano-node 5, so that the distance between each (1-4) is maintained, but the distance between 4 and 5 is shortened below the threshold. In some embodiments, the nano-micro interface or another external device stores and/or accesses the mapping of the nano-nodes and sends signals or otherwise causes the nano-nodes to move as desired based on the mapping.

In some embodiments, nano-nodes are in a family or cluster. In some embodiments, the family includes one or more nano-routers. The nano-node family is able to include nano-nodes of a same type or nano-nodes of different types. The nano-node family is able to be used to maintain a nano-node chain, so that each nano-node is able to communicate via hops to a nano-router. The nano-nodes of the nano-node family are able to have the same family ID, to facilitate communication. For example, if a communication is sent to nano-nodes, it is able to be sent only to nano-nodes with a specific family ID.

In some embodiments, the nano-nodes 100 and/or nano-routers 102 communicate with many nano-micro interfaces 104 and/or other devices external to the body. For example, one or more sensors in a sneaker/shoe are able to acquire information such as number of steps or amount of pressure placed on different parts of the shoe, and at the same time, nano-nodes 100 are able to monitor/detect strain within the user's body such as at ligaments, tendons, muscles and/or bones. Furthering the example, one or more nano-nodes 100 configured with/as pressure sensors are able to be embedded in a muscle, ligament, tendon, and/or bone to acquire a second set of information. Then, using the information from the shoe and the information from the nano-nodes 100, real-time analysis is able to be performed to determine if the user is moving incorrectly, if the shoe has issues, and/or any other potential problems or benefits. Similarly, nano-nodes 100 and/or another nano-micro interface 104 are able to monitor heart activity in synchronization with the shoe sensors and/or nano-nodes 100 in the leg (or foot, back, elsewhere).

In another example, one or more air sensors communicate with one or more nano-nodes 100 in the lungs, one or more nano-nodes 100 in/near the heart, and the shoe sensors to retrieve respiration information (e.g., for asthmatics and/or people with heart conditions).

In another example, nano-nodes 100 configured to detect body inflammation and/or allergic reactions, and food sensors (e.g., a smart refrigerator for analyzing/knowing food ingredient information) are able to communicate with each other or a central unit to alert users of possible allergy issues and/or other food intolerances.

In some embodiments, the physical area network includes additional monitoring sensors such as ECG, EMG, EEG, chemical sensors (e.g., sweat, glucose, saliva), optical sensors (e.g., oximetry, tissue properties), and/or other types of sensors. In some embodiments, the nano-nodes 100 and/or other components are able to be configured into devices/sensors such as a defibrilator, sleep analyzer, and/or any other device.

In an example, one or more nano-nodes 100 detect blood sugar levels, and if the blood sugar level is above a threshold, an implanted insulin pump injects insulin.

In some embodiments, the physical area network maintains a history of a user's information (e.g., health information), maintains a record of medicines taken, provides alerts to the user to take medication, provides commentary/advice based on acquired information (e.g., heart rate monitoring), contacts doctors/emergency personnel/family when an emergency situation is detected (e.g., dangerous heart arrhythmia) and/or performs other tasks/services.

In some embodiments, the physical area network is able to be implemented with gaming. The information acquired by the physical area network is processed/analyzed, and then that information is translated to affect gameplay. Additionally, the gameplay information is able to be processed/analyzed, and then that information is translated to affect the physical area network. For example, a database is able to correlate information/actions related to the physical area network with gameplay, and vice versa. For example, to assist children in dealing with a disease, a game is able to correspond with physical area network information. Furthering the example, if a child is fighting cancer, a cancer game is able to be implemented on a gaming console, a smart television, a smart phone, a personal computer, a virtual reality device, an augmented reality device, and/or any other computing device. The gameplay involves the child fighting video game cancer cells (or another illness), and as the nano-nodes perform treatment on the child, the game provides power-ups for the child and/or other features/bonuses. In some embodiments, to prompt the child to take medication or receive treatment, the game includes bonuses upon detection of the mediation/treatment being received. For example, when a nano-node deploys a medication, a signal is sent to the nano-micro interface which sends a signal/command/data to the gameplay to give the user a bonus such as extra power, an extra life, an extra weapon/ammunition, unlocking a secret stage, and/or any other bonus. In some embodiments, the game content is unrelated to the illness. Any other interactions between the physical area network and the game/gameplay are possible. The game is able to affect the physical area network, and the physical area network is able to affect the game. In some embodiments, the game is not related to an illness but another interaction based on the nano-nodes. For example, the gameplay is a racing game to distract a person while the nano-nodes travel through the user's gastrointestinal system. In another example, the game is utilized while nano-nodes are utilized with medical imaging. In another example, the game provides a game version of the user's body, and the user is able to control where a nano-node moves on the game, which also controls where the nano-node in the user's body moves. In addition to interacting with the game and the nano-nodes, other items components, devices, and/or equipment are able to be utilized such as food, sneakers, sporting equipment and clothing. For example, a video game incorporates information/analysis based on food intake, exercise and the current weather, where nano-nodes determine calories and/or the type of food ingested, nano-nodes in sneakers or "connected" sneakers communicate the user's exercise routine, and the user's clothing includes sensors to detect humidity and temperature or the weather information is received from an online source. Furthering the example, the information acquired enables the user to compete against friends in an online health/exercise competition or simply keep track of the information. In some embodiments, the game displayed is not interactive; rather, it is a video showing the user a representation of what is occurring within the user. For example, a cartoon video of germs being blasted by nanonodes is shown to a child who is ill, where the cartoon is based on the events taking place inside the child.

Figure 15:
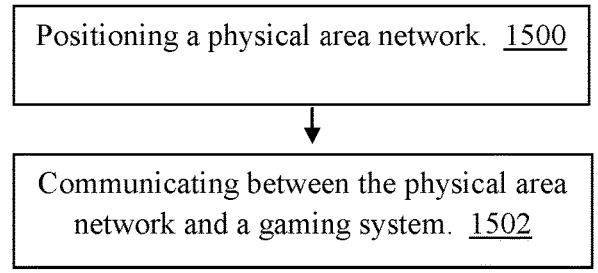
FIG. 15 illustrates a flowchart of a method of implementing gaming with a physical area network according to some embodiments.

FIG. 15 illustrates a flowchart of a method of implementing gaming with a physical area network according to some embodiments. In the step 1500, the physical area network is positioned. In the step 1502, the physical area network communicates with a gaming system. The gaming system is able to be a gaming console, a smart phone (or other smart device), a headset display, and/or another device capable of being used for gaming. Communicating between the physical area network and the gaming system is able to include an initialization/configuration step. For example, the physical area network is synchronized with the gaming system. Additionally, specific details about the physical area network (such as how many nano-nodes, types of nano-nodes, positions of nano-nodes, illness, medications available for use and/or being used, and others) and/or the gaming system (such as the type of gaming system, player information, number of players, gaming information, and others) are able to be communicated to each other or another device. For example, the game to be played may be based on the physical area network configuration. Furthering the example, if a user is battling lung cancer, that information is able to be provided to the gaming system via the physical area network (e.g., nano-nodes communicate their location and/or a server communicates the user's current illness and/or location of the nano-nodes; actions taken by the nano-nodes are communicated such as attacking the cancer, deploying medication and others). For example, a game programmed to function on the gaming system includes code which is able to accept/retrieve data from the physical area network, and then apply that data in the game (e.g., receive data from nano-nodes on how many have deployed medication and how many still have medication to be deployed which shows up on the GUI of the game as ammunition used/remaining). Furthering the example, when a nano-node deploys medication, the nano-node sends a signal that the medication has been deployed, and then nano-micro interface is able to translate the signal into a command/data to send to the gaming device to affect the gameplay such as shooting a germ with medication in the game. In another example, the game includes code which is able to send data to the physical area network, and then the physical area network applies that data (e.g., user presses Button A which triggers a shot of medication on the game and also sends a command to the physical area network to release medication). In another example, the user moves his spaceship from the leg to the heart searching for illnesses in the game which sends a command to trigger one or more nano-nodes to move from the leg to the heart of the user. In some embodiments, the gameplay replicates the current state of the user (e.g., based on the detected size of the real-life cancerous mass, the gameplay includes a cancerous mass of a same/comparable size). Additionally, as the nano-nodes attack the real-life cancerous mass, the gameplay shows the game cancerous mass being attacked. In some embodiments, the gameplay attempts to replicate reality, and in some embodiments, the gameplay cartoonizes reality. In some embodiments, the gameplay completely changes reality such as while a cancerous mass is being attacked by medicine, the gameplay involves an enemy spacecraft being attacked by heroes' ships. In some embodiments, the gameplay is a one way communication (either nano-nodes to gaming device or vice versa), or the gameplay is a two-way communication. For example, when the nano-nodes perform an action, a signal is sent to the gaming device to show a corresponding action. In another example, when a user performs an action on a gaming device, a signal is sent to the nano-nodes to perform a corresponding action. In an example of two-way communication, the user is able to play the game which causes nano-node actions, and as the nano-nodes perform actions, the nano-nodes communicate back to the game to cause a corresponding action in the game. The nano-nodes are able to include safeguards to prevent a user from doing harm. For example, in a gameplay where the user is shooting a gaming illness with medication, the corresponding action is medication being provided by the nano-nodes, but once a desired amount of medication has been provided, the nano-nodes do not provide any more medication. Communicating between the devices is able to be implemented in any manner. For example, the physical area network collects data as described herein (e.g., nano-nodes collect internal body information), communicates the data as described herein, and either: communicates directly to a gaming system, communicates to a nano-micro interface which communicates (including translates, if necessary) with the gaming system, or communicates with another device which communicates (including translates, if necessary) with the gaming system. In some embodiments, fewer or additional steps are implemented. In some embodiments, the order of the steps is modified.

In some embodiments, the nano-nodes 100, nano-routers 102, and/or other components are made of biocompatible materials such as platinum, gold, or titanium.

In some embodiments, the nano-micro interface 104 is able to communicate with/over one or more networks (e.g., the Internet, cellular networks), including social networks such as Facebook®. In some ways, communicating health information over the networks is a form of social networking. By receiving information from many people (any number up to billions or more), mass information is able to be gathered and analyzed. The information is able to be anonymized. Moreover, the information is able to be grouped/separated based on any characteristic(s) such as age, gender, sex, race, body features, location, illness, genetic information, and others to perform analysis such as detecting trends. Even more specific details are able to be included in the analysis such as genetic information, location information, height, weight, age, eye color, right/left-handed, hair color, baldness, exercise history, personality, family history, family environment, personal activities such as sleep schedule/quality, diet, drugs/alcohol consumption, occupation, habits, exercise, scheduling, and/or any other specific details. In some embodiments, social networking is used for comparison purposes. For example, health information (acquired using the physical area network) from contacts in a user's social network is aggregated and/or compared. Since contacts may have similarities (e.g., from the same location), by analyzing their health information, commonalities may be determined. During or after the analysis is performed, the results are able to be provided to the contacts (and actions are able to be taken). For example, if cancer is detected in one of the contacts, a message is able to be sent to the other contacts of that contact that someone in their social network has cancer. In some embodiments, the message is sent to each contacts' physical area network to automatically initiate additional cancer monitoring (by those contacts' physical area networks and/or other precautions). Similarly, if contacts live near each other, a medical illness could be based on local environmental factors, and the detection of an illness results in a communication with the contacts.

In some embodiments, the health information from others is used to perform treatment or preemptive treatment. For example, nano-nodes in User A detect an illness based on certain factors/symptoms detected by the nano-nodes and/or nano-micro interface, and the information gathered (including the factors/symptoms/illness) is communicated to others (e.g., through the Internet) including User B. User B's physical area network receives the information and determines that similar symptoms are occurring in User B, so the physical area network takes preemptive steps to prevent the illness from advancing. In another example, based on social networking of physical area networks of contacts, early, middle and later symptoms are determined for illness X, where the symptoms vary slightly depending on the person, and effective treatments also vary slightly depending on the person, so users are matched based on similarities with the contacts, and the physical area network of the users implement appropriate treatments based the specific information from contacts. Exemplary actions taken by the physical area network include suggesting specific exercises, diets, and/or medications; deploying nano-nodes to investigate the user further to determine the progress of a disease/treatment; and/or deploying nano-nodes to take action to fight the disease such as providing medication and/or otherwise treating the disease. In some embodiments, the response to the preemptive actions is also collected to further analyze to determine if better treatments are available and/or which ones work. The social networking analysis is able to be implemented in any manner including using artificial intelligence to determine patterns. The social networking analysis is able to be implemented using a structured tree where each branch leads to a different treatment option including the results/success rates of each option.

In some embodiments, in some embodiments, information shared via social networking includes specific details of the physical area network such as nano-nodes/nano-routers (e.g., brand, type, quantity, location such as a map of nano-node/nano-router distribution/orientation), so that others are able to have a similar physical area network. For example, if a specific physical area network works well at detecting potential illnesses for Contact A or Group X, then the physical area network information is transmitted and downloaded/accessed by Contact B or Group Y, and their physical area network is able to re-orient itself to match the successful orientation/configuration. In some embodiments, if desired components are not part of the current physical area network (e.g., Contact B does not have Sensor J), then the physical area network is able to automatically purchase the desired components (e.g., via nano-micro interface automatically placing an order) or provide information to someone (e.g., Contact B or Contact B's physician) to place an order or prescription. The shared information is able to include exercise information, diet information, injury information, illness information and/or other information, so that contacts are able to replicate another contact's regimen. Where the physical area network tracks specific exercise movements, the physical area network is able to provide the contact with information of the movements such as giving names of the exercises or displaying a video showing the movements. For example, Contact A runs for 3 miles in 25 minutes–the distance and time are able to be shared, in addition to elevation changes, the surface for running (e.g., asphalt, dirt), a map of the run, heart rates, current weight, strains on joints/muscles, and/or any other relevant information. The information is able to be acquired by the physical area network in any manner such as a pedometer tracking the distance, the nano-micro interface tracking the time and heart rate and generating a map using GPS and mapping information, smart sneakers for detecting the type of surface or determining the type of surface based on compression amounts of the sneaker, and nano-nodes positioned near joints and muscles to detect strain. Then, Contact B is able to duplicate the trip or run a comparable trip. In some embodiments, the shared information is able to be compared for analysis purposes and/or competitive purposes. For example, if the race tracks/trips are not exactly the same, based on analysis, variations are able to be accounted for (e.g., if Contact A's trip had more elevation gain than Contact B's trip, then Contact A is given a slight bonus such as reduced time by X seconds to account for the differential).

In another example, injury information is able to be shared automatically. For example, for athletes, if nano-nodes detect a player has a concussion or tears a ligament or breaks a bone, the information is able to be automatically shared with the team doctor, the league and/or other entities.

In some embodiments, user-enabled privacy settings are implemented. For example, Contact A shares everything with the world, so he allows all of his information to be shared with anyone. Contact B shares information only with those in his private network. Contact Z does not want much shared, so only exercise information is shared such as time and distance without any of the health statistics/data. Any HIPPA standards (or other standards/requirements) are able to be followed/implemented.

In some embodiments, illness information is shared. For example, to protect against the spread of the flu, once nano-nodes detect a flu virus or other symptoms such as a fever, the user's school, work and/or other contacts are able to be automatically contacted. Similarly, once the user's levels (e.g., temperature or detection of eradication of illness) have returned to normal, the school, work, contacts are able to be contacted again to enable a safe return. This would significantly minimize the spread of infectious diseases and drastically reduce medical costs as well as missed time from work. The information sent is able to be as detailed or limited as desired (e.g., Student X has Y illness with Z symptoms, or Student X is unable to attend school today)—configurable either by the user or the receiver of the data (e.g., student or school limits information). In some embodiments, when a person has an illness, an illness status on the user's social network page changes (e.g., from healthy to sick or sick with X illness). In some embodiments, an emoji or other graphical representation changes to reflect the health of a user.

Figure 16:
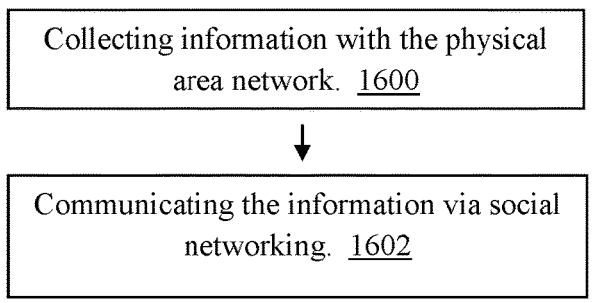
FIG. 16 illustrates a flowchart of a method of utilizing a physical area network with social networking according to some embodiments.

FIG. 16 illustrates a flowchart of a method of utilizing a physical area network with social networking according to some embodiments. In the step 1600, the physical area network collects information. As described herein, the physical area network collects health information using nano-nodes, nano-routers and the nano-micro interface and/or additional information. In the step 1602, the physical area network communicates the information via social networking. For example, symptoms, treatment and side effect information as well as other information is able to be transmitted/gathered via social networking to further medical advancements. In some embodiments, fewer or additional steps are implemented. In some embodiments, the order of the steps is modified.

In some embodiments, nano-nodes are configured to detect concussions and/or other head injuries. For example, nano-nodes are positioned in or navigate to the CSF (or otherwise near the brain) surrounding the brain. Using nano-nodes (e.g., physical nanosensors) as described herein, it is able to be detected if the brain has been injured from pressing against the inside of the skull. For example, analysis is performed to determine a threshold amount of pressure/force of the brain pressing against the skull before an injury occurs, and if that amount of pressure/force is detected by a nanonode, then it is determined that the user has a concussion. In some embodiments, levels of concussion are able to be determined such as: below a first threshold, between the first threshold and a second threshold, and above the second threshold. In some embodiments, the nano-nodes are strategically placed to surround the brain to ensure that a hit from any angle is detected. In another example, the nano-nodes are placed at/near the top, bottom, left, right, front and back of the brain. The nano-nodes communicate as described herein either to other nano-nodes, nano-routers, or a nano-micro interface. In some embodiments, the information communicated is as simple as an indication of "concussion detected" which is able to be represented as a single bit, or more information including the specific pressure/force detected as well as the location, time information and/or how many nano-nodes detected the pressure/force above a threshold. For example, if 1 nano-node of a group of 10 nano-nodes detects a force above a threshold, but the other 9 do not, then an alert may not be triggered. In some embodiments, when 1 nano-node in the brain area detects a pressure/force above a threshold, all of the nano-nodes in the brain area transmit their information to enable mapping of the injury. For example, the nano-nodes on the top, bottom left and right all report low pressure/force information, but the nano-nodes in the front and back report pressure/force information above a threshold. In some embodiments, various nano-nodes are developed and deployed such as nano-nodes that are triggered at different levels of pressure/force/impact. For example, one set of nano-nodes are triggered by a low amount of force (e.g., above a first threshold but below a second threshold), a second set of nano-nodes are triggered by a higher amount of force (e.g., above the second threshold but below a third threshold), and a third set of nano-nodes are triggered by a highest amount of force (e.g., above the third threshold). Then, depending on which nano-nodes are triggered and send a signal, it is able to be determined how strong the impact was. Any number of nano-nodes with different trigger amounts are able to be used. The concussion information is able to be communicated (e.g., from the nano-micro interface) to any other device such as a referee device, a coach's device, and/or a server for data analysis. Other ways of detecting a concussion are able to be implemented by the physical area network, such as detecting swelling in the brain, detecting changes in color of the brain, detecting a biochemical change in the CSF, determining motor skill issues such as instability of the user, and determining eye movement irregularities.

In some embodiments, the physical area network includes eye-wear such as glasses, goggles, AR glasses/goggles, VR glasses/goggles, contact lenses, or AR or VR contact lenses. In an exemplary implementation, the physical area network includes VR goggles which include one or more cameras or sensors to view the user's eyes (e.g., one camera per eye), and when a user plays a VR game/program, the cameras monitor the user's eyes to detect any anomalies such as issues stemming from a head injury such as a concussion. In some embodiments, the eye-wear is used in conjunction with the video game which is used in conjunction with the nano-nodes. For example, the nano-nodes in/on the user's head/helmet detect a possible concussion, then cameras in the user's helmet detect eye movement that also indicates a concussion, so with the two indicators, it is more likely that a concussion has occurred. In another example, after a concussion has been detected, the protocol includes the user playing a VR video game, and while playing, cameras in the VR headset monitor the user's eyes to detect eye issues, and/or the video game communicates with the nano-nodes in the user's brain to send and receive information related to the head injury.

Figure 17:
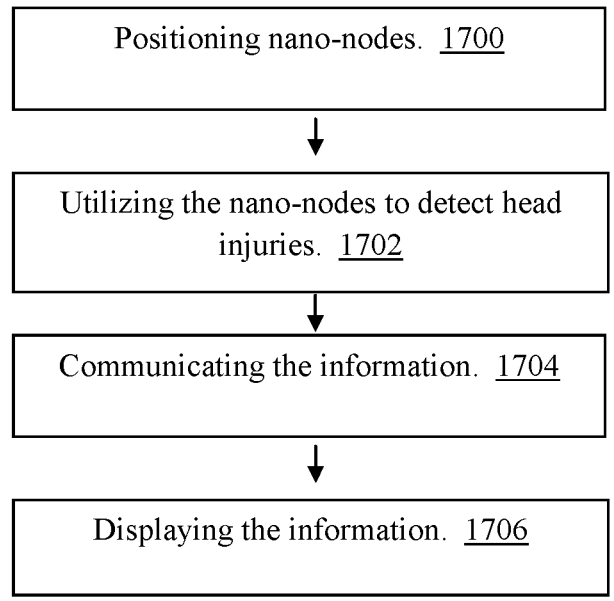
FIG. 17 illustrates a flowchart of utilizing nano-nodes to detect a concussion according to some embodiments.

FIG. 17 illustrates a flowchart of utilizing nano-nodes to detect a concussion according to some embodiments. In the step 1700, nano-nodes are positioned. For example, nano-nodes are injected into position and/or travel to a desired location such as various locations in the CSF surrounding the brain. Furthering the example, the nano-nodes are physical nano-sensors configured to detect pressure/force such as impact pressure/force. In some embodiments, the nano-nodes are positioned outside the user's body (e.g., on the scalp, in the hair, on the inner layer of the helmet or other headgear, inside the helmet/headgear, on the outer layer of the helmet/headgear). In the step 1702, the nano-nodes detect/measure the force, including a location of the impact (e.g., based on which nano-node is triggered and the location of the nano-node). In the step 1704, the nano-nodes communicate information (e.g., being triggered, location information, amount of force detected) to another device such as the nano-micro interface. In the step 1706, the device displays the information. For example, the device flashes red when a concussion has been detected. In another example, more specific data is displayed such as the location of the impact/injury and the amount of force. In addition to or instead of displaying information, an action is able to be taken such as anti-inflammation medication is able to be applied to the injured area using the nano-nodes. In some embodiments, fewer or additional steps are implemented. In some embodiments, the order of the steps is modified.

Figure 18:
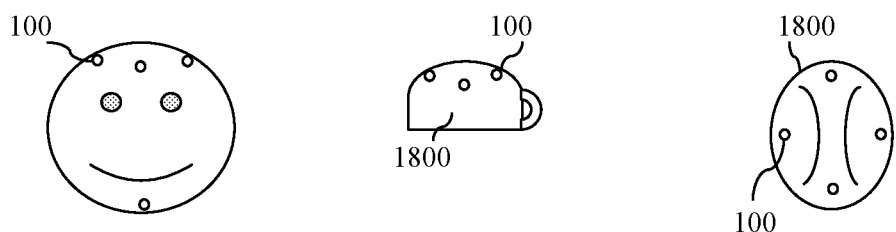
FIG. 18 illustrates a diagram of utilizing nano-nodes to detect a concussion according to some embodiments.

FIG. 18 illustrates a diagram of utilizing nano-nodes to detect a concussion according to some embodiments. As shown in the left-most figure, the nano-nodes 100 are able to be placed on a user's scalp, in the user's hair, under the skin, or further internally (e.g., in the CSF). The nano-nodes 100 are able to be placed anywhere on the head/body to detect head injuries such as concussions such as anywhere on the head including the face (e.g., nose, cheeks, chin) and/or the top of the head/scalp/hair. In some embodiments, the nano-nodes are placed in a specific pattern such as a ring, a checkerboard pattern, or 4 (or more) opposite points (one toward the front, one toward the back, one on the left and one on the right or more on at each location).

In the middle figure, nano-nodes 100 are able to be placed on an outer surface of a helmet 1800. The nano-nodes 100 are able to be placed in any pattern as described herein. In some embodiments, the nano-nodes 100 are embedded in the helmet (e.g., in the cushioning). In some embodiments, the nano-nodes 100 are included in the paint or are positioned on the outside of the helmet in another manner. The helmet 1800 is able to be any helmet such as a sporting helmet (e.g., football, hockey, baseball), a bike helmet, a ski/snowboard helmet, wrestling headgear, or any other type of helmet/headgear/headwear. In some embodiments, instead of a helmet, the nano-nodes are positioned on another type of headwear such as a hat.

In the right-most figure, the underside of a helmet 1800 is shown with nano-nodes 100 positioned on the surface of the inside of the helmet 1800, where the helmet 1800 touches the user's head. The nano-nodes 100 are able to be positioned in a pattern as described herein.

In some embodiments, the nano-micro interface is configured to communicate with an external device to cause that external device to react/respond (e.g., nano-micro interface communicates with a self-ointing toothbrush to put toothpaste on the toothbrush).

In some embodiment, quantum computing is utilized to process the physical area network information. For example, for encryption, a server utilizes quantum computing to encrypt and decrypt data.

In some embodiments, the physical area network is able to be used to implement remote monitoring of a subject such as an adult, child, baby, pet, livestock, or any other animal. Vital signs such as heart rate, blood pressure, breathing/oxygen levels, location, surroundings (light, dark, temperature), medical issues (fever, illness, germs) are able to be monitored and communicated to a parent/owner device and/or other devices.

In some embodiments, the nano-nodes are deployed/implemented based on conditions. For example, as a person ages, the potential issues change. Furthering the example, it is important to monitor for breast cancer when a woman reaches a specified age, so based on the age change, the nano-nodes monitor for different conditions. Similarly, when a woman is pregnant, it is important to monitor for different things as the pregnancy continues, so the nano-nodes receive varying instructions depending on the time/month of the pregnancy. Similarly, prostate cancer is generally a concern for older men, so although nano-nodes are able to detect cancer, the nano-nodes are able to re-position themselves near the prostate or begin to attempt to detect prostate cancer when the user reaches an age threshold.

As described herein, the physical area network is able to be used to track exercise information. The exercise information is able to be tracked in conjunction with other information such as food intake, illnesses/conditions, and/or any other bodily functions, environmental factors/functions, and/or any other information.

Figure 19:
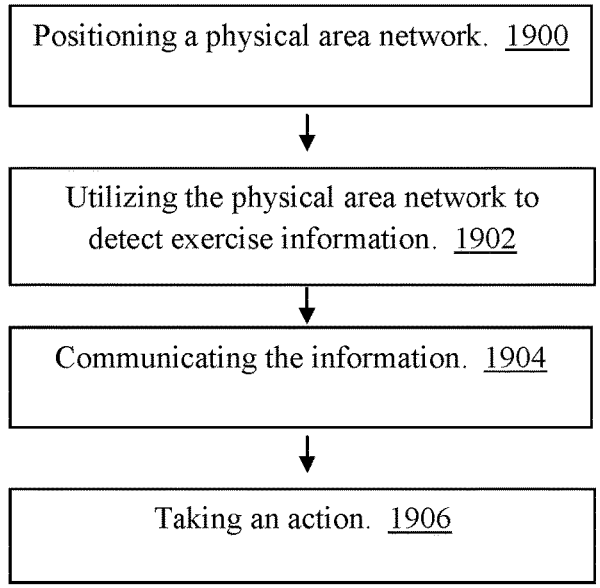
FIG. 19 illustrates a flowchart of a method of tracking exercise according to some embodiments.

FIG. 19 illustrates a flowchart of a method of tracking exercise according to some embodiments. In the step 1900, the physical area network is positioned. For example, nano-nodes and nano-routers are injected, inhaled, and/or ingested, and a nano-micro interface (e.g., smart watch or smart clothing) is put on. In the step 1902, the physical area network detects exercise information. For example, any of the following is able to be detected (and more): motion information, any strains or stress, vital signs, specific training information, body information, medical information, and/or environmental information. In the step 1904, the exercise information is communicated (e.g., from nano-nodes to the nano-micro interface to a server device, or vice versa). In the step 1904, the physical area network takes an action. For example, an asthmatic person may need steroids for his lungs, and based on detecting lung inflammation or low oxygen levels, the nano-nodes are able to provide the steroids or trigger an alert that an asthma attack is imminent or occurring. In another example, taking an action includes displaying information on the nano-micro interface and/or another display device. In some embodiments, fewer or additional steps are implemented. In some embodiments, the order of the steps is modified.

In some embodiments, various items/parts are linked such as shoes+heart; watch+heart; shoes+heart+watch; food+heart; food+head; food+gut, and so on.

In some embodiments, an accelerometer (or another device) within the nano-micro interface or another device is used to determine a user's body position in conjunction with symptoms. Additional information is able to be captured and analyzed as well such as time of day, day of year, location information, and/or any other information. For example, the nano-micro interface determines that a user is lying down, and nano-nodes in the mouth and/or throat detect that acid reflux is occurring (e.g., by detecting pH). In some embodiments, the accelerometer or other device is used to determine which exercise is occurring. The information and/or other sensor information is then able to be used to determine the user's technique and compare the user's technique with proper techniques and send to a screen/wearable glasses/lenses/goggles to show the user the proper technique. The user's technique is displayed as an outline on a video of a proper technique, or the property technique is displayed as an outline on a video of the user's technique. In another example, the proper technique is overlaid using augmented reality.

In some embodiments, one or more sensors (or nano-nodes) are positioned in/on equipment to help with learning/practicing techniques. For example, a sensor/nano-node is included in a baseball bat, golf club, sneakers, basketball, baseball, football, soccer ball, hockey stick, puck, leotard, floor, and/or other sporting equipment. Furthering the example, the equipment sensor is used in conjunction with nano-nodes within the user's body and/or on the user's body (e.g., smart clothing) to determine: is the bat level, is the golf club going at the correct arc/angle, hips moving at right time, and other motions/movements. In an example, smart clothing is able to detect a change in capacitance between the skin and one or more electrodes of the clothing. The equipment sensors are able to be used in conjunction with the nano-micro interface and/or nano-nodes for analyzing the user's movements/motion. For example, the sensor in the equipment tracks movement including timestamps, and nano-nodes also track movement or other body data (e.g., heart rate, blood pressure) (including timestamps). Furthering the example, as a player starts to swing, it is time t=0s, and data is acquired at increments of 1 second or other intervals such as tenths of a second, 1 millisecond, 1 microsecond, or 1 nanosecond. At t=0s, a player's heart rate is detected using the physical area network (e.g., nano-nodes or nano-micro interface), and the player's starting position is determined (e.g., the angle of the bat is detected using a sensor of the bat, and the player's smart clothing detects the position of the player's elbow, hips and other body parts). The nano-nodes are able to be positioned at the player's joints, muscles, tendons, bones and/or other parts, to detect pressure, strain, pulling and/or other possible injuries. At time t=1.2s, it is detected that the player's bat is coming through the ball at an improper angle, and nano-nodes (pressure sensors) in the player's wrist detect that there is strain on the player's tendons. The information such as timing information, bat speed and angle information, and/or nano-node information is collected and then processed to determine any issues or a proper technique, and the raw data and/or processed data are able to be presented to the user or others by alert or in a report. In some embodiments, the physical area network communicates with a device with a display (e.g., screen or VR googles) and/or an audible indicator is used. For example, when the player swings improperly and/or strain is detected on a player's body part, it is indicated (e.g., red flashing on the screen). When the player swings again and swings properly, it is also indicated (e.g., green flashing on the screen). All of the data points of the swing, at all of the time intervals, are able to be acquired, analyzed, and processed in real-time, including providing an output usable to avoid injury and/or improve a motion. In some embodiments, the visual display includes a simulation indicating what to correct. For example, a visual representation of the correct swing is overlaid on a visual representation of the player's swing.

In another example, a baseball includes one or more sensors which are able to measure spin, velocity, angle, and/or any other information of the ball. Additionally, a nano-micro interface (e.g., smart bracelet or watch) on the thrower's wrist is able to detect the thrower's arm motion using accelerometers, gyroscopes, and/or other components. Nano-nodes in the thrower's body are able to be used to detect movement, strain (e.g., muscles/bones/ligaments in/on the shoulder, wrist, elbow, arm) and/or any vital statistics/information. The information from the baseball, wearable device, and/or the nano-nodes is able to be collected and analyzed to determine the thrower's throwing motion to determine if there are any imperfections which are causing excess strain on the thrower's body or causing the throw to be inefficient. The thrower is also able to be alerted when his throw is off. For example, an audible/visual alert is triggered when the throw angle is wrong. In some embodiments, an AR or VR device is worn to show the thrower a proper angle or alert the thrower of poor form. In some embodiments, the AR or VR device shows the proper form in real-time or after. In some embodiments, the data is recorded and reviewable later. The data is able to be collected and analyzed including when an injury occurs to further improve future analysis.

Figure 20:
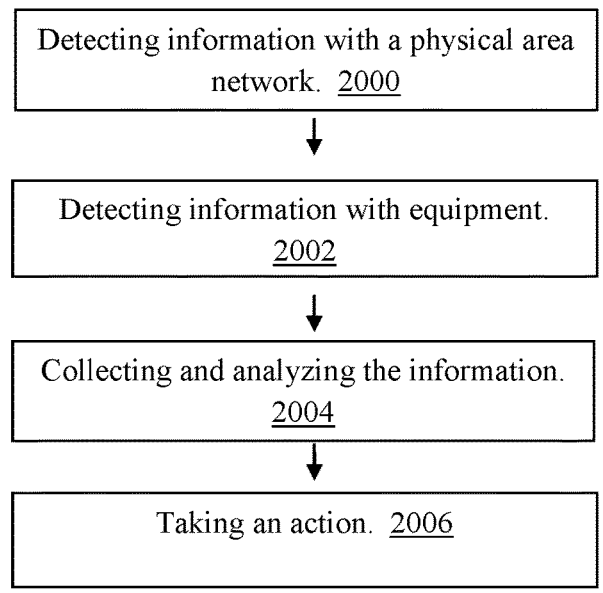
FIG. 20 illustrates a flowchart of a method of utilizing the physical area network with additional equipment according to some embodiments.

FIG. 20 illustrates a flowchart of a method of utilizing the physical area network with additional equipment according to some embodiments. The additional equipment is able to be sporting equipment, work equipment, medical equipment, cooking equipment, housework equipment, electrical equipment, computer equipment, a vehicle, and/or any other equipment. In the step 2000, a physical area network detects information. For example, the physical area network detects strain and/or stresses on the user's body and/or vital signs. In the step 2002, the equipment detects information. For example, speeds, angles of motion, motions of the equipment are detected. In some embodiments, the physical area network and the equipment communicate for the detection of information. In the step 2004, the information from the physical area network and/or equipment is collected and analyzed. For example, the nano-micro interface and/or a server receive the information and analyze the information to determine issues, correct behaviors, incorrect behaviors, and/or any other analysis. In the step 2006, an action is taken. For example, an alert is displayed when strain above a threshold is detected. In another example, a video is displayed showing the correct motion. In some embodiments, fewer or additional steps are implemented. In some embodiments, the order of the steps is modified. For example, the steps 2000 and 2002 are able to occur simultaneously.

Figure 21:
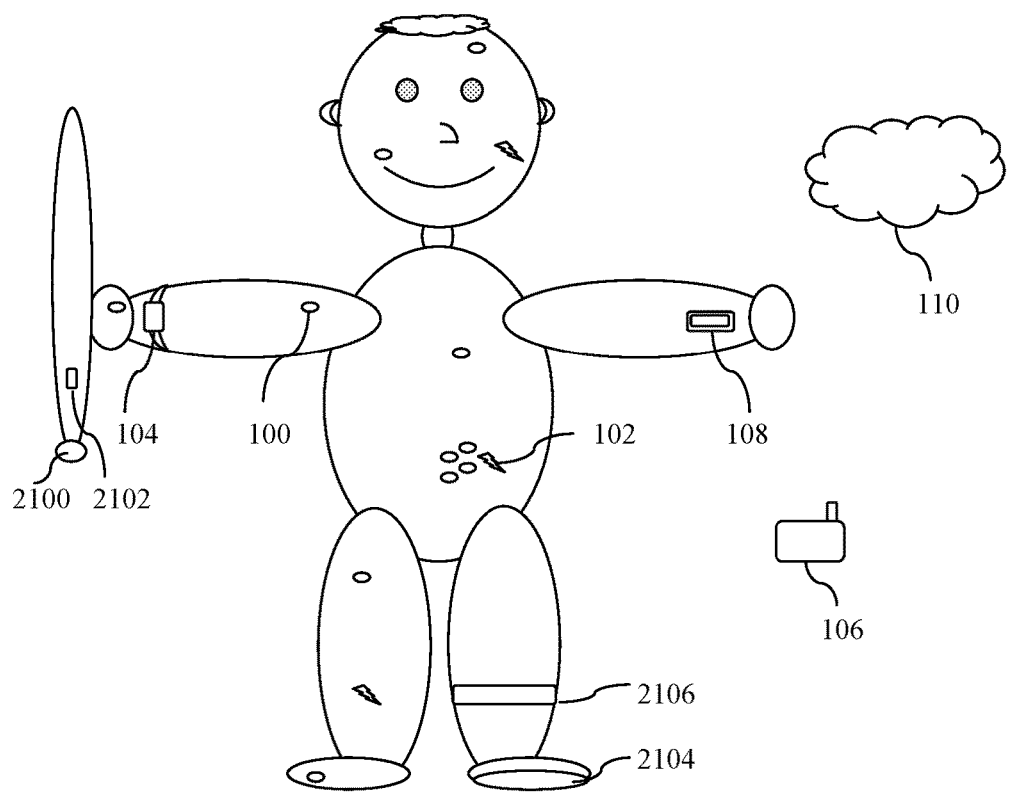
FIG. 21 illustrates a user with a physical area network and equipment configured to communicate with the physical area network according to some embodiments.

FIG. 21 illustrates a user with a physical area network and equipment configured to communicate with the physical area network according to some embodiments. As described in FIG. 1, the physical area network includes one or more nano-nodes 100, one or more nano-routers 102, one or more nano-micro interfaces 104, and/or one or more control units 106, one or more electronic tattoos 108. In some embodiments, the physical area network is able to communicate via a network 110 (e.g., the Internet or an intranet) or using peer-to-peer communication.

The equipment 2100 includes one or more sensors 2102 positioned anywhere in/on the equipment 2100. As described herein, the equipment 2100 is able to include a baseball bat, baseball, hockey stick, football, soccer ball, and so on including other types of equipment. The sensors 2102 are able to communicate the sensed information to the physical area network or another device. In some embodiments, the physical area network includes wearable clothing such as a smart shoe 2104 and/or smart clothing 2106 (e.g., smart band).

The physical area network and the equipment are able to work together to detect information to assist a user in whatever activity the user is doing such as a sport, hobby, and/or work.

As described herein, the physical area network is able to be used to detect and/or treat any type of symptom/illness/conditions such as cancer, diabetes, heart disease, high cholesterol, arrhythmia, anxiety, depression, acid reflux, asthma, cold, flu, gastrointestinal issues, and/or pregnancy.

The physical area network is able to be used to determine if an illness is viral or bacterial. By detecting RNA/DNA matches using nano-nodes to capture the virus/bacteria, the type of illness (viral/bacterial) is able to be detected as well as the specific illness (cold/flu/mononucleosis). In some embodiments, determining the type of illness includes utilizing one or more nano-nodes to determine the size of the virus or bacteria, and based on the size, they are able to be distinguished (e.g., bacteria are larger than viruses). In some embodiments, determining the type of illness includes utilizing one or more nanosensors to determine chemical reactions of the bacteria or virus to distinguish them (e.g., bacteria react to an antibacterial, whereas viruses do not). In some embodiments, the nano-nodes monitor the virus/bacteria movements, and based on distinguishing characteristics, a virus or bacteria is able to be determined (e.g., bacteria reproduce on their own, whereas viruses attach to a cell to reproduce). Antigens are also able to be used for detection. By determining the difference, treatment options may vary. For example, if it is determined that an illness is bacterial, then a user is alerted and/or an antibacterial medication is deployed automatically.

Figure 22:
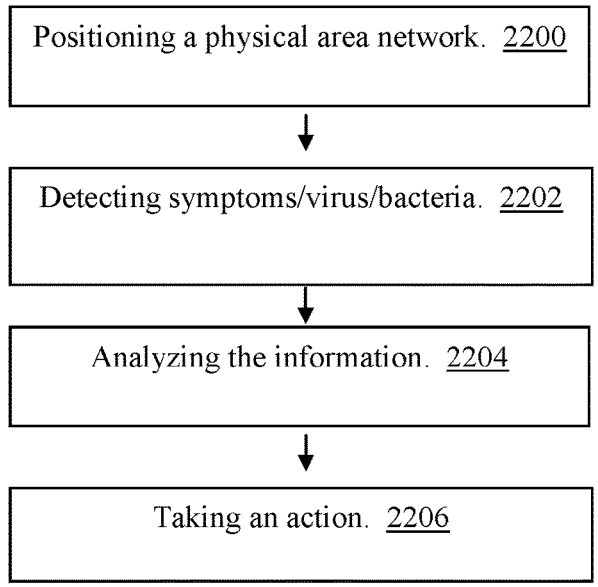
FIG. 22 illustrates a flowchart of a method of utilizing the physical area network to detect an illness according to some embodiments.

FIG. 22 illustrates a flowchart of a method of utilizing the physical area network to detect an illness according to some embodiments. In the step 2200, the physical area network is positioned on/in the user. In the step 2202, the physical area network detects symptoms and/or virus/bacteria. For example, the nano-nodes and/or nano-micro interface are able to detect an elevated temperature. In another example, the nano-nodes are able to locate a virus or bacteria using specific nanosensors. In the step 2204, the information detected is analyzed. As described herein, based on the detection, a type of illness is able to be determined. In an example, if the virus or bacteria is captured and/or identified, then further analysis may not be implemented, but if a virus or bacteria is not detected, a diagnosis may be available based on symptoms detected and/or other information (e.g., genetic history, environmental information). In the step 2206, an action is taken such as alerting the user that the user has illness X. In another example, if an elevated temperature is detected, the nano-nodes are informed to investigate further in an attempt to determine the type of illness by capturing the virus or bacteria. In some embodiments, fewer or additional steps are implemented. In some embodiments, the order of the steps is modified.

In some embodiments, the physical area network is used to monitor a user while sleeping. The nano-nodes and/or the nano-micro interface of the physical area network monitor the user's movement, brain activity, heart rate, blood pressure, blood sugar, rapid eye movement, and/or any other information. The physical area network detects user movement during sleep. In some embodiments, the physical area network communicates with a bed which is capable of detecting movement. The information collected from the physical area network and/or other devices is able to be analyzed to determine causes of sleep issues/disorders such as blood pressure spikes while sleeping, blood sugar drops while sleeping, triggers for dreams, and/or any other symptoms/effects. Food information is able to be correlated as well such as the user having sleep issues or nightmares after eating triggering foods. Trends and causes are able to be determined by analysis of the food, sleep and/or other activity information.

Figure 23:
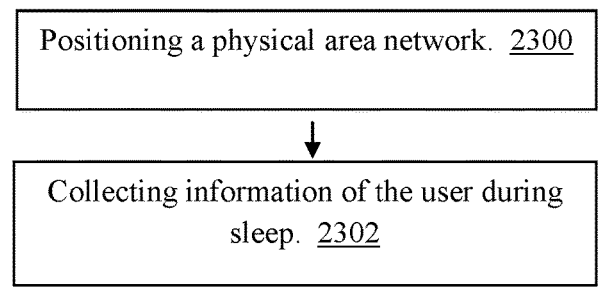
FIG. 23 illustrates a flowchart of a method of monitoring sleep of a user according to some embodiments.

FIG. 23 illustrates a flowchart of a method of monitoring sleep of a user according to some embodiments. In the step 2300, the physical area network is positioned. In the step 2302, the physical area network monitors a user's sleep. Monitoring the user's sleep is able to include monitoring movement, brain activity, heart rate, blood pressure, blood sugar, rapid eye movement, and/or any other information. The nano-nodes are able to monitor internal information, and the nano-micro interface (e.g., smart watch or smart clothing) is able to monitor external information. In some embodiments, the information is analyzed per night or over a period of time to determine patterns. In some embodiments, fewer or additional steps are implemented. In some embodiments, the order of the steps is modified.

In some embodiments, the physical area network is able to be used as a permanent, automatic doctor guidance system. The physical area network is able to detect symptoms/illnesses automatically. Additionally, a user is able to input symptoms (e.g., achy) via a GUI or voice commands on a smart watch/phone, and the nano-nodes are able to investigate based on the input symptoms. The physical area network is able to access medical information (source information) which is updated continuously or on a regular basis (e.g., daily) based on medical information gathered from other physical area networks and/or other sources. The symptoms (and other medical information e.g., medical history, age, sex, environmental factors) are then able to be compared with the source information to determine an illness of the user (or potential illnesses of the user). The diagnosis is able to be provided to the user (e.g., displayed on the user's smart phone), including potential/recommended treatment options and/or other information. In some embodiments, medical information is provided manually (e.g., by a doctor). For example, a local/remote doctor reviews the symptom/medical information from the physical area network and provides a diagnosis.

Figure 24:
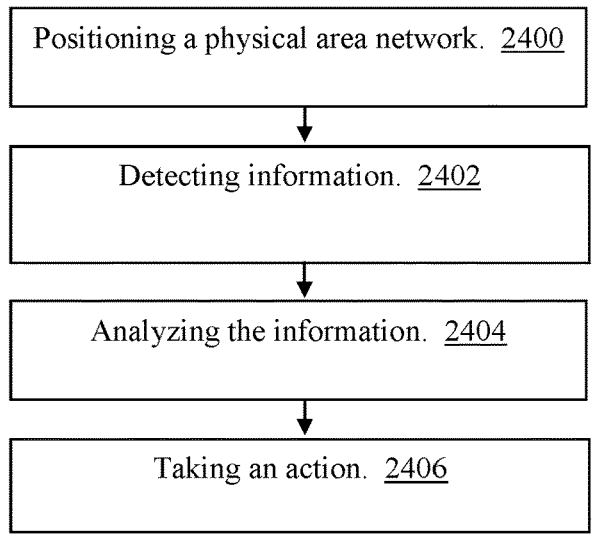
FIG. 24 illustrates a flowchart of a method of utilizing the physical area network as a remote monitoring system/automatic doctor implementation according to some embodiments.

FIG. 24 illustrates a flowchart of a method of utilizing the physical area network as a remote monitoring system/automatic doctor implementation according to some embodiments. In the step 2400, the physical area network is positioned. In the step 2402, the physical area network monitors the user including detecting movement, detecting symptoms/illnesses, analyzing food intake, analyzing exercise, detecting vital signs, determining location information, and/or any detection/monitoring. In the step 2404, the information acquired by monitoring and/or other information is analyzed (e.g., matching symptoms with stored information of possible illnesses). In the step 2406, an action is taken. For example, the physical area network is able to alert the user, communicate/alert a contact of the user such as a family member, friend and/or doctor. In another example, in a remote monitoring implementation, the location/health information of the user is able to be sent to another (e.g., to a parent), so that the parent is aware of the user's health status and location. In some embodiments, fewer or additional steps are implemented. In some embodiments, the order of the steps is modified.

In some embodiments, nano-nodes are equipped with a variety of medications. For example, a first set of nano-nodes contain Med X, a second set of nano-nodes contain Med Y and a third set of nano-nodes contain Med Z. One of the medications or a combination of medications are tried, and then the physical area network detects any physical response/side effects (e.g., accelerated heart rate, weight loss, anxiety, allergic reaction and many others). If no negative effects are detected and/or the illness responds to the medication, then the other medications are not utilized (and the nano-nodes may move to be disposed of such as in the bladder or colon). If negative effects are detected and/or the illness is not responding to the medication, then that medication is stopped and possibly moves to be disposed of, and another medication or combination of medications is tried, and the process is repeated.

In some embodiments, the nano-nodes include motion sensors. Utilizing arranged carbon nano-tubes, tiny movements and changes in gravity are able to be sensed which would indicate motion. Upon detecting motion, an action is able to be taken such as deploying a medication, mobilizing nano-nodes to attack a blockage, or sending a signal to the nano-micro interface to trigger an alert.

Artificial intelligence is able to be used with the physical area network in any manner/implementation. For example, artificial intelligence is able to be implemented on a server to process data received from one or more physical area networks. Furthering the example, as data is received, the data is analyzed, and using artificial intelligence the system is able to learn by detecting patterns, comparing data/symptoms, and/or any other manner. In another example, artificial intelligence is able to be utilized in deploying the physical area network such as sending signals to the nano-nodes in where to move to, what to look for/detect, and/or providing any other instructions. The artificial intelligence is able to be implemented in any manner such as a neural network.

In some embodiments, the nano-nodes are used to monitor blood alcohol content levels and are able to send a signal via a nano-router to an external device such as a wearable device or a phone. As described herein, chemical sensors are able to be used to detect various chemicals such as ethanol and/or other alcohols.

Figure 25:
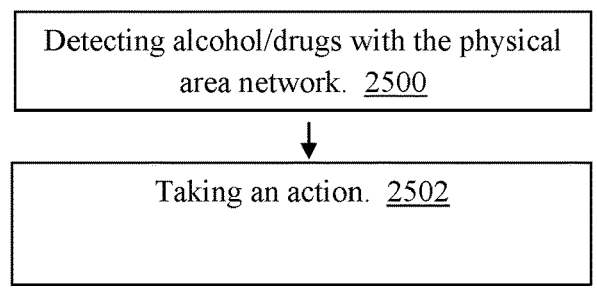
FIG. 25 illustrates a flowchart of detecting alcohol/drugs using the physical area network according to some embodiments.

FIG. 25 illustrates a flowchart of detecting alcohol/drugs using the physical area network according to some embodiments. In the step 2500, the physical area network detects alcohol/drugs in the user's system. Detecting the alcohol/drugs is able to be implemented in any manner such as using nano-sensors configured to acquire specific items such as alcohol or specific drugs. An amount of alcohol or drugs in a person's system is able to be calculated based the concentration detected using many nano-nodes and determining how many detect alcohol/drugs and how many do not. In some embodiments, other/additional factors are used to detect alcohol/drugs such as irregular movement, accelerated and/or irregular heartbeat, other impaired actions, and/or any other physiological triggers; detecting the alcohol/drugs using a mouth-based sensor; and/or other information. For example, the accelerometer of the nano-micro interface is able to detect irregular movements by the user (e.g., based on the accelerometer). In another example, the nano-nodes are able to detect physiological changes such as an accelerated heartbeat based on the use of certain drugs. In the step 2502, an action is taken. The action taken may be to automatically call for a driver (e.g., contact a self-driving vehicle including sending current location information), the police, or an ambulance; automatically disable the user's vehicle; alert the user of their condition (e.g., blood alcohol content above the legal limit) and/or any other action.

In some embodiments, the physical area device is able to communicate with a self-driving vehicle. For example, if a user has a medical issue or any other need/desire, the physical area network is able to communicate (e.g., smart watch sends a communication including GPS or other location information) to a self-driving car service or a ride-share service. The physical area network is also able to communicate to any other driving service (e.g., a ride-share service with a human driver).

In some embodiments, one or more nano-nodes in a user's bloodstream are configured to measure the diameter or a change in diameter of an artery and/or vein. Measuring the diameter is implemented by measuring the distance from one wall to the opposite wall by the nano-node tracking the distance as it moves. In another example, the diameter is measured by sending and detecting electrical pulses and detecting if the pulse is able to reach the artery/vein wall. The diameter is able to be determined based on the strength of the electrical pulse. In another example, the diameter is measured by sending signals and detecting reflections of the signals off the artery/vein wall, and based on the speed of the reflections, a distance is able to be determined. In some embodiments, antenna (or other transceivers) are located in opposite directions (e.g., one pointed left, one pointed right and/or one pointed forward, one pointed backward). In addition to detecting the diameter, the location of the nano-node in the body is determined. Determining the location is able to be based on detected oxygen levels, salinity levels, size of the diameter, and/or any other information. The location is able to be sent from the nano-micro interface which knows the location of the nano-node. The location is also able to be determined using an external device capable of scanning and detecting the nano-node and then communicating the location to the appropriate location (e.g., the nano-micro interface). In some embodiments, the nano-nodes (or specialized nano-nodes) are configured to break up plaque and/or employ medications to remove, cut, dissolve, break up, chisel, and/or burn the plaque. For example, the nano-node includes an acid which is capable of dissolving the plaque. In another example, the nano-node includes a blade/chisel capable of breaking up the plaque. In another example, the nano-nodes locate blood clots and break them up using the mechanisms described herein. In another example, the nano-nodes vibrate rapidly to beak up the plaque. Blood clots are able to be found by having many nano-nodes within a body, and when a nano-node reaches an obstruction or partial obstruction (e.g., by detecting a narrowing of a vein/artery diameter), the nano-node is able to take action.

Figure 26:
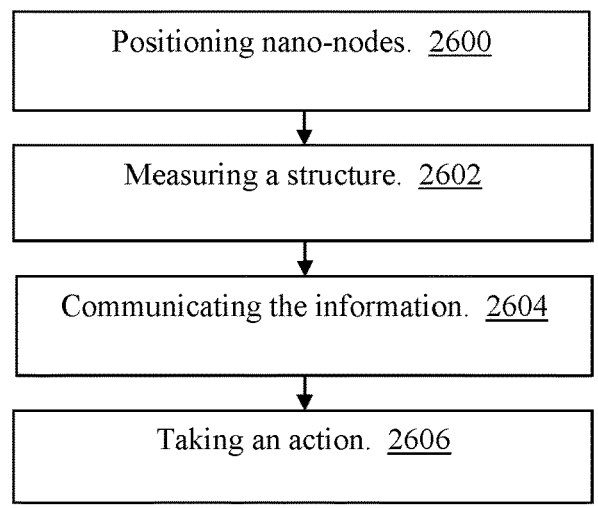
FIG. 26 illustrates a flowchart of a method of detecting sizes of structures within a user's body according to some embodiments.

FIG. 26 illustrates a flowchart of a method of detecting sizes of structures within a user's body according to some embodiments. In the step 2600, nano-nodes are positioned in the user (e.g., injected into a user's vein). In some embodiments, the nano-nodes navigate after initial positioning. In the step 2602, the nano-nodes measure a structure (e.g., a vein, artery or other structure). In the step 2604, the nano-nodes communicate the measurement information (e.g., to a nano-micro interface). In the step 2606, the nano-nodes take an action. For example, after indicating that an artery is partially blocked, the nano-nodes receive a signal and take action to break up the blockage (e.g., with tools, heat, medication). In some embodiments, fewer or additional steps are implemented. In some embodiments, the order of the steps is modified.

Figure 27:
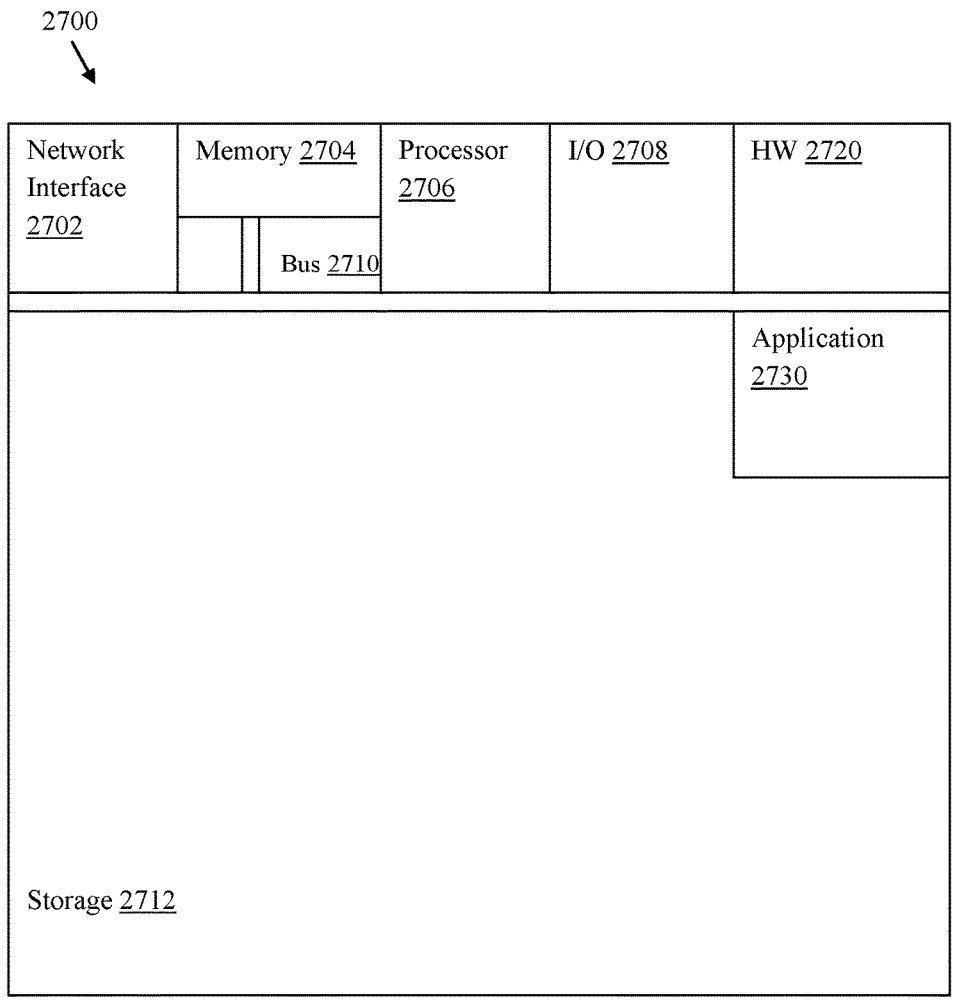
FIG. 27 illustrates a block diagram of an exemplary computing device configured to implement aspects of the physical area network according to some embodiments.

FIG. 27 illustrates a block diagram of an exemplary computing device configured to implement aspects of the physical area network according to some embodiments. For example, the computing device 2700 communicates with the physical area network (e.g., via the nano-micro interface). In another example, the computing device 2600 is the nano-micro interface. The computing device 2700 is able to be used to acquire, store, compute, process, communicate and/or display information including, but not limited to, text, images, videos and audio. In some examples, the computing device 2700 is able to be used to monitor information, process the information, perform analysis and/or provide a recommendation. In general, a hardware structure suitable for implementing the computing device 2700 includes a network interface 2702, a memory 2704, a processor 2706, I/O device(s) 2708, a bus 2710 and a storage device 2712. The choice of processor is not critical as long as a suitable processor with sufficient speed is chosen. The memory 2704 is able to be any conventional computer memory known in the art. The storage device 2712 is able to include a hard drive, CDROM, CDRW, DVD, DVDRW, flash memory card, solid state drive or any other storage device. The computing device 2700 is able to include one or more network interfaces 2702. An example of a network interface includes a network card connected to an Ethernet or other type of LAN. The I/O device(s) 2708 are able to include one or more of the following: keyboard, mouse, monitor, display, printer, modem, touchscreen, touchpad, speaker/microphone, voice input device, eye detection, infrared detection, hologram detection, button interface, hand-waving, body-motion capture, touchless 3D input, joystick, remote control, brain-computer interface/direct neural interface/brain-machine interface, camera, and other devices. In some embodiments, the hardware structure includes multiple processors and other hardware to perform parallel processing. Physical area network application(s) 2730 used to perform the monitoring, processing, analyzing and providing are likely to be stored in the storage device 2712 and memory 2704 and processed as applications are typically processed. More or fewer components shown in FIG. 27 are able to be included in the computing device 2700. In some embodiments, physical area network hardware 2720 is included. Although the computing device 2700 in FIG. 27 includes applications 2730 and hardware 2720 for implementing the physical area network, the physical area network is able to be implemented on a computing device in hardware, firmware, software or any combination thereof. For example, in some embodiments, the physical area network applications 2730 are programmed in a memory and executed using a processor. In another example, in some embodiments, the physical area network hardware 2720 is programmed hardware logic including gates specifically designed to implement the physical area network.

In some embodiments, the physical area network application(s) 2730 include several applications and/or modules. Modules include a monitoring module for monitoring information, a processing module for processing (e.g., converting) information, an analysis module for analyzing information and a providing module for providing a recommendation. In some embodiments, modules include one or more sub-modules as well. In some embodiments, fewer or additional modules are able to be included. In some embodiments, the applications and/or the modules are located on different devices. For example, a device performs monitoring, processing, and analyzing, but the providing is performed on a different device, or in another example, the monitoring and processing occurs on a first device, the analysis occurs on a second device and the providing occurs on a third device. Any configuration of where the applications/modules are located is able to be implemented such that the physical area network is executed.

In some embodiments, a specialized computing device is utilized to implement the physical area network. In some embodiments, the specialized computing device utilizes a dedicated processor and/or dedicated memory for processing physical area network information. In some embodiments, instructions are stored on the specialized computing device to enable the computing device to efficiently analyze information to provide physical area network recommendations.

Examples of suitable computing devices include, but are not limited to nano-devices, micro-devices, a personal computer, a laptop computer, a computer workstation, a server, a mainframe computer, a handheld computer, a personal digital assistant, a pager, a telephone, a fax machine, a cellular/mobile telephone, a smart appliance, a gaming console, a digital camera, a digital camcorder, a camera phone, a smart phone/device (e.g., a Droid® or an iPhone®), a portable music player (e.g., an iPod®), a tablet (e.g., an iPad®), a video player, an e-reader (e.g., Kindle™), a DVD writer/player, an HD (e.g., Blu-ray®) or ultra high density writer/player, a television, a copy machine, a scanner, a car stereo, a stereo, a satellite, a DVR (e.g., TiVo®), a smart watch/jewelry, smart devices, a home entertainment system or any other suitable computing device.

The user described herein is able to be any animal (e.g., human, pet, livestock) or plant.

Any of the steps described herein are able to be performed in real-time.

Although some implementations and/or embodiments have been described related to specific implementations and/or embodiments, and some aspects/elements/steps of some implementations and/or embodiments have been described related to specific implementations and/or embodiments, any of the aspects/elements/steps, implementations and/or embodiments are applicable to other aspects/elements/steps, implementations and/or embodiments described herein.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method of treating cancer comprising:
positioning, in or on a user, a set of nano-nodes, wherein a surface of each nano-node in the set of nano-nodes is encapsulated with one or more plasma membrane-associated components, and wherein the one or more plasma membrane-associated components are derived from a cancer cell, and further wherein at least one nano-node of the set of nano-nodes includes a plurality of chambers, each chamber of the plurality of chambers for storing at least part of a medication; and
activating an immune response against the cancer cell in the user, thereby treating the cancer.

2. The method of claim 1 further comprising deploying the at least part of the medication using the set of nano-nodes to treat the cancer.

3. The method of claim 1 wherein the at least part of the medication in each chamber of the at least one nano-node is an inert component of the medication which is activated when mixed upon release.

4. The method of claim 1 wherein positioning the set of nano-nodes includes utilizing at least one nano-node configured for autonomous movement.

5. The method of claim 1 wherein positioning the set of nano-nodes further comprises including a magnetic component in at least one nano-node of the set of nano-nodes which is attracted by a magnetic device.

6. The method of claim 1 wherein at least one nano-node of the set of nano-nodes includes one or more sensors.

7. The method of claim 1 wherein the set of nano-nodes comprise at least one decoy nano-node.

8. The method of claim 1 wherein at least one nano-node of the set of nano-nodes includes a polypyrrole nanowire configured for providing movement of the nano-node.

* * * * *